United States Patent [19]

McConnell

[11] 4,132,780
[45] Jan. 2, 1979

[54] AZIDE-METAL SALT FORMULATIONS FOR CONTROL OF FUNGI AND NEMATODES

[75] Inventor: William C. McConnell, Flat Rock, N.C.

[73] Assignee: PPG Industries, Inc., Pittsburgh, Pa.

[21] Appl. No.: 821,432

[22] Filed: Aug. 3, 1977

Related U.S. Application Data

[63] Continuation of Ser. No. 624,357, Oct. 21, 1975, abandoned.

[51] Int. Cl.$^2$ .............................................. A01N 11/00
[52] U.S. Cl. .................... 424/127; 424/128; 424/131; 424/144; 424/145; 424/147; 424/151; 424/153; 424/154; 424/287; 424/288; 424/289; 424/295; 424/317
[58] Field of Search ............... 424/127, 226, 131, 144, 424/145, 147, 153, 154, 151, 128, 287, 288, 289, 295, 317

[56] References Cited

U.S. PATENT DOCUMENTS 3,812,254   5/1974   McConnell .................... 424/226

OTHER PUBLICATIONS

Chemical Abstracts, vol. 72 (1970), p. 77971m.
Gregory, T., "Uses & Applications of Chemicals & Related Materials" (1939), p. 354, Reinhold Pub. Co.

Primary Examiner—V. D. Turner
Attorney, Agent, or Firm—Robert J. Grassi

[57] ABSTRACT

Disclosed are novel azide compositions comprised of one or more azides in combination with one or more metal salts. The azides are hydrazoic acid, alkali metal azides, or alkaline earth metal azides and the metal salts are fluorides, bromides, chlorides, carbonates, sulfates, phosphates, nitrates, hydroxides, oxides, formates, acetates, propionates, oxalates, malates, citrates, butyrates, lactates, or tartrates of the metal ions: iron, aluminum, nickel, manganese (II), cobalt (II), zinc, tin (II), or magnesium. These compositions exhibit useful agricultural properties and are used to control plant pests such as pathogenic fungi, or nemas by applying the composition to the region where the pests reside.

72 Claims, No Drawings

AZIDE-METAL SALT FORMULATIONS FOR CONTROL OF FUNGI AND NEMATODES

This is a continuation of application Ser. No. 624,357, filed Oct. 21, 1975, now abandoned.

BACKGROUND OF THE INVENTION

1. Field of the Invention

This invention concerns azide compositions, particularly, compositions containing hydrazoic acid one or more alkali metal azides or alkaline earth metal azides in combination with one or more metal salts having metal ions of iron, aluminum, cobalt (II), nickel, tin (II), magnesium, zinc, or manganese (II), and anions of bromide, chloride, fluoride, carbonate, hydroxide, nitrate, oxide, phosphate, sulfate, formate, acetate, propionate, butyrate, oxalate, citrate, malate, lactate, or tartrate. These compositions are especially useful for controlling plant pests such as pathogenic fungi, pathogenic nemas, and other pathogenic microorganisms, as well as, augmenting the growth of beneficial micro-flora; such as *Trichoderma viride*.

These compositions exhibit useful agricultural properties; such as a decreased release rate of azide ion, a reduced phytotoxicity to plants, and an extended active soil life.

2. Description of the Prior Art

The prior art is replete with azides; examples of which are: $Cr(N_3)_3$, $Zn(N_3)_2$, $H_3[Cr(N_3)_6]$, and $[Ni(NH_3)_2](N_3)_2$. A large number of these azides are listed in "Hydrazoic Acid," *Kirk-Othomer Encyclopedia of Chemical Technology*, 1951; *Mellor's Inorganic and Theoretical Chemistry*, (New York, NY 1940), 8: 344; "The Metallic Azides," *Mellor's Comprehensive Treatise on Inorganic and Theoretical Chemistry*, (New York, NY 1967), Vol. III, Supplement II, Nitrogen (Pt. II), Section XIX; L. F. Audrieth, *Chemical Review* 15, 1934, pages 169–224; and *Hydrazoic Acid and the Metal Azides*, Report 1551-TR, Project 8-07-11-440, U.S. Army Engineer Research and Development Laboratories Corporation of Engineers, October 28, 1958.

Azides in compositions containing certain metal salts are disclosed in the following patents. U.S. Pat. No. 3,741,585 discloses a nitrogen gas producing composition which contains alkali metal azides, alkaline earth metal azides, and aluminum together with ferrous sulfide, ferrous iodide, and stannic iodide; U.S. Pat. No. 3,865,660 discloses a gas generating composition containing an alkali metal azide and anhydrous chromic chloride as an oxidizer. U.S. Pat. No. 3,342,577 discloses a fertilizer granule sealed by petroleum coatings to which a very small amount of sodium azide or potassium azide is added, together with other agents; such as boric acid, or copper chloride, etc. U.S. Pat. No. 3,883,373 discloses a gas gennerating composition of an alkali, or alkaline earth metal azide, an oxidizing compound, an oxide such as silica or alumina, and optionally a metal such as silicon or aluminum.

The herbicidal, fungicidal, nematocidal, and pesticidal properties of azides, particularly sodium, potassium, and ammonium azide have been recognized, see U.S. Pat. Nos. 3,376,125, 3,376,126, and 3,376,127.

SUMMARY OF THE INVENTION

In accordance with this invention novel biologically active compositions are provided which contain one or more azides in combination with one or more selected metal salts. Such compositions are especially beneficial for agricultural uses in that they exhibit a decreased release rate of azide ion, a reduced phytotoxicity and an extended soil life.

The azide content of these compositions is provided by hydrazoic acid, alkali metal azides and/or alkaline earth metal azides. Appropriate metal salts are those containing metal ions of iron, cobalt (II), nickel, manganese (II), aluminum, magnesium, zinc, or tin (II), and anions of bromide, chloride, fluoride, carbonate, hydroxide, nitrate, oxide, phosphate, sulfate, formate, acetate, propionate, butyrate, oxalate, citrate, malate, lactate, or tartrate. These azide-metal salt compositions are free from heavy metal ions such as copper, silver, mercury, lead, gold, etc., which cause formation of explosive compounds, and other anions or compounds such as perchlorate, chlorate, iodide, oxidizers, or equivalents which cause decomposition. The metal ions of the metal salt may be chelated. The ratio of the mole equivalents of azide ions to mole equivalents of the metal ion in these compositions is within the range of 0.01 to 8.0. Novel liquid and novel solid compositions are contemplated. Solid compositions typically are comprised of inert granules such as clay granules impregnated with both the azide and metal salt. These compositions are used to control plant pests; such as pathogenic fungi, pathogenic bacteria, pathogenic nemas, and other pathogenic microorganisms; such as *Sclerotium rolfsii* and *Alternaria solani*, as well as to augment the growth of beneficial micro-flora, e.g., *Trichoderma viride* which are natural biological control agents. The compositions are applied in an effective amount to the region where the plant pest is located to control these plant pests.

DESCRIPTION OF THE PREFERRED EMBODIMENTS

General Makeup Of The Compositions

The compositions of this invention encompass both solid compositions and liquid compositions, which are comprised of the metal salts described herein and azides described herein.

a. Suitable Metal Salts

The metal salts are those which have one or more metal ions in aluminum, iron (II), iron (III), cobalt (II), magnesium, tin (II), manganese (II), or zinc, and one or more anions of chloride, bromide, fluoride, hydroxide, carbonate, nitrate, oxide, phosphate, sulfate, formate, acetate, malate, propionate, butyrate, oxalate, citrate, lactate, or tartrate.

Examples of suitable metal salts for forming these compositions are:

| | |
|---|---|
| aluminum fluoride | $AlF_3$ |
| aluminum bromide | $AlBr_3$ |
| aluminum chloride | $AlCl_3(Al_2Cl_6)$ |
| aluminum chloride, hexahydrate | $AlCl_3 \cdot 6H_2O$ |
| aluminum nitrate, nonohydrate | $Al(NO_3)_3 \cdot 9H_2O$ |
| aluminum metaphosphate | $Al(PO_3)_3$ |
| aluminum orthophosphate | $AlPO_4$ |
| aluminum sulfate | $Al_2(SO_4)_3$ |
| aluminum sulfate, hydrate | $Al_2(SO_4)_3 \cdot 18H_2O$ |
| aluminum hydroxide | $Al(OH)_3$ |
| cobalt (II) chloride, dihydrate | $CoCl_2 \cdot 2H_2O$ |
| cobalt (II) chloride, hexahydrate | $CoCl_2 \cdot 6H_2O$ |
| cobalt (II) citrate | $Co_3(C_6H_5O_7)_2 \cdot 2H_2O$ |
| cobalt (II) formate | $Co(CHO_2)_2 \cdot 2H_2O$ |
| cobalt (II) fluoride | $CoF_2$ |
| cobalt (II) hydroxide | $Co(OH)_2$ |
| cobalt (II) bromide | $CoBr_2$ |
| cobalt (II) bromide, hexahydrate | $CoBr_2 \cdot 6H_2O$ |
| cobalt (II) nitrate | $Co(NO_3)_2 \cdot 6H_2O$ |
| cobalt (II) oxalate | $CoC_2O_4$ |
| cobalt (II) oxalate, dihydrate | $CoC_2O_4 \cdot 2H_2O$ |
| cobalt (II) orthophosphate | $Co_3(PO_4)_2$ |

| | |
|---|---|
| cobalt (II) orthophosphate, dihydrate | Co$_3$(PO$_4$)$_2$ · 2H$_2$O |
| cobalt (II) orthophosphate, octahydrate | Co$_3$(PO$_4$)$_2$ · 8H$_2$O |
| cobalt (II) propionate | Co(C$_3$H$_5$O$_2$) · 3H$_2$O |
| cobalt (II) acetate, hydrate | Co(C$_2$H$_3$O$_2$)$_2$ · 4H$_2$O |
| cobalt (II) carbonate, basic | 2CoCO$_3$ · Co(OH)$_2$ · H$_2$O |
| cobalt (II) chloride | CoCl$_2$ |
| cobalt (II) sulfate | CoSO$_4$ |
| cobalt (II) sulfate, heptahydrate (natural bieberite) | CoSO$_4$ · 7H$_2$O |
| cobalt (II) sulfate, monohydrate | CoSO$_4$ · H$_2$O |
| cobalt (II) tartrate | CoC$_4$H$_4$O$_6$ |
| iron (II) acetate | Fe(C$_2$H$_3$O$_2$)$_2$ · 4H$_2$O |
| iron (III) acetate, basic | FeOH(C$_2$H$_3$O$_2$)$_2$ |
| iron (II) carbonate (natural siderite) | FeCO$_3$ |
| iron (II) carbonate, hydrate | FeCO$_3$ · H$_2$O |
| iron (II) chloride (natural lawrencite) | FeCl$_2$ |
| iron (II) chloride, dihydrate | FeCl$_2$ · 2H$_2$O |
| iron (II) chloride, tetrahydrate | FeCl$_2$ · 4H$_2$O |
| iron (III) chloride (natural molysite) | FeCl$_3$ or Fe$_2$Cl$_6$ |
| iron (III) chloride, hydrate | FeCl$_3$ · 2½ H$_2$O |
| iron (III) chloride, hexahydrate | FeCl$_3$ · 6H$_2$O |
| iron (III) formate | Fe(CHO$_2$)$_3$ · H$_2$O |
| iron (II) fluoride | FeF$_2$ |
| iron (III) fluoride | FeF$_3$ |
| iron (II) hydroxide | Fe(OH)$_2$ |
| iron (III) hydrosulfate (iron tetrasulfate - natural rhomboklas) | Fe$_2$O$_3$ · 4SO$_3$ · 9H$_2$O |
| iron (II) bromide | FeBr$_2$ |
| iron (II) bromide, hexahydrate | FeBr$_2$ · 6H$_2$O |
| iron (III) bromide | FeBr$_3$ |
| iron (III) bromide, hexahydrate | FeBr$_3$ · 6H$_2$O |
| iron (II) lactate | Fe(C$_3$H$_5$O$_3$)$_2$ · 3H$_2$O |
| iron (III) lactate | Fe(C$_3$H$_5$O$_3$)$_3$ |
| iron (III) malate | Fe$_2$(C$_4$H$_4$O$_5$)$_3$ |
| iron (II) nitrate | Fe(NO$_3$)$_2$ · 6H$_2$O |
| iron (III) nitrate | Fe(NO$_3$)$_3$ · 6H$_2$O |
| iron (III) nitrate | Fe(NO$_3$)$_3$ · 9H$_2$O |
| iron (II) oxalate | FeC$_2$O$_4$ · 2H$_2$O |
| iron (III) oxalate | Fe$_2$(C$_2$O$_4$)$_3$ · 5H$_2$O |
| iron (III) oxide, hydrate | Fe$_2$O$_3$XH$_2$O |
| iron (III) orthophosphate | FePO$_4$ · 2H$_2$O |
| iron (II) sulfate (natural szomolnikite) | FeSO$_4$ · H$_2$O |
| iron (III) sulfate | Fe$_2$(SO$_4$)$_3$ |
| iron (II) sulfate, heptahydrate (natural melanterite) | FeSO$_4$ · 7H$_2$O |
| iron (II) sulfate, pentahydrate (natural siderotil) | FeSO$_4$ · 5H$_2$O |
| iron (II) sulfate, tetrahydrate | FeSO$_4$ · 4H$_2$O |
| magnesium bromide | MgBr$_2$ |
| magnesium bromide, hexahydrate | MgBr$_2$ · 6H$_2$O |
| magnesium acetate | Mg(C$_2$H$_3$O)$_2$ |
| magnesium acetate, tetrahydrate | Mg(C$_2$H$_3$O)$_2$ · 4H$_2$O |
| magnesium carbonate (natural magnesite) | MgCO$_3$ |
| magnesium carbonate, basic (natural hydromagnesite) | 3MgCO$_3$ · Mg(OH)$_2$ · 3H$_2$O |
| magnesium carbonate, pentahydrate (natural lansfordite) | MgCO$_3$ · 5H$_2$O |
| magnesium carbonate, trihydrate (natural nesquehonite) | MgCO$_3$ · 3H$_2$O |
| magnesium chloride | MgCl$_2$ |
| magnesium chloride, hexahydrate (natural bischofite) | MgCl$_2$ · 6H$_2$O |
| magnesium citrate, nonohydrate | MgHC$_6$H$_5$O$_7$ · 5H$_2$O |
| magnesium formate | Mg(CHO$_2$)$_2$ · 2H$_2$O |
| magnesium fluoride | MgF$_2$ |
| magnesium hydroxide | Mg(OH)$_2$ |
| magnesium hydroxide (natural brucite) | Mg(OH)$_2$ |
| magnesium lactate | Mg(C$_3$H$_5$O$_3$) · 3H$_2$O |
| magnesium nitrate, dihydrate | Mg(NO$_3$)$_2$ · 2H$_2$O |
| magnesium nitrate, hexahydrate | Mg(NO$_3$)$_2$ · 6H$_2$O |
| magnesium oxalate | MgC$_2$O$_4$ · 2H$_2$O |
| magnesium oxide | MgO |
| magnesium oxide (natural periclase) | MgO |
| magnesium orthophosphate | Mg$_3$(PO$_4$)$_2$ |
| magnesium orthophosphate | Mg$_3$(PO$_4$)$_2$ · 22H$_2$O |
| magnesium orthophosphate mono-H (natural newberyite) | MgHPO$_4$ · 3H$_2$O |
| magnesium orthophosphate, mono-H, heptahydrate | MgHPO$_4$ · 7H$_2$O |
| magnesium orthophosphate, octahydrate (natural bobierite) | Mg$_3$(PO$_4$)$_2$ · 8H$_2$O |
| magnesium orthophosphate, tetrahydrate | Mg$_3$(PO$_4$)$_2$ · 4H$_2$O |
| magnesium pyrophosphate | Mg$_2$P$_2$O$_7$ |
| magnesium sulfate | MgSO$_4$ |
| magnesium sulfate, heptahydrate Epon salt, (natural epsomite) | MgSO$_4$ · 7H$_2$O |
| magnesium sulfate, monohydrate (natural kieserite) | MgSO$_4$ · H$_2$O |
| magnesium d-tartrate | MgC$_4$H$_4$O$_6$ · 5H$_2$O |
| magnesium d-tartrate, hydrogen | Mg(HC$_4$H$_4$O$_6$)$_2$ · 4H$_2$O |
| manganese (II) bromide | MnBr$_2$ |
| manganese (II) bromide, tetrahydrate | MnBr$_2$ · 4H$_2$O |
| manganese (II) carbonate | MnCO$_3$ |
| manganese (II) carbonate (natural rodochrosite) | MnCO$_3$ |
| manganese dichloride (natural scacchite) | MnCl$_2$ |
| manganese dichloride, tetrahydrate | MnCl$_2$ · 4H$_2$O |
| manganese (II) citrate | Mn$_2$(C$_6$H$_5$O$_7$)$_2$ |
| manganese (II) formate | Mn(CHO$_2$)$_2$ · 2H$_2$O |
| manganese (II) fluoride | MnF$_2$ |
| manganese (II) hydroxide (natural pyrochroite) | Mn(OH)$_2$ |
| manganese (II) nitrate | Mn(NO$_3$)$_2$ · 4H$_2$O |
| manganese (II) lactate | Mn(C$_3$H$_5$O$_3$)$_2$ · 3H$_2$O |
| manganese (II) oxalate, dihydrate | MnC$_2$O$_4$ · 2H$_2$O |
| manganese (II) orthophosphate | Mn$_3$(PO$_4$)$_2$ |
| manganese (II) orthophosphate (natural reddingsite) | Mn$_3$(PO$_4$)$_2$ · 3H$_2$O |
| manganese (II) orthophosphate, dihydrogen | Mn(H$_2$PO$_4$)$_2$ · 2H$_2$O |
| manganese (II) orthophosphate, monohydrogen | MnHPO$_4$ · 3H$_2$O |
| manganese (II) pyrophosphate | Mn$_2$P$_2$O$_7$ |
| manganese (II) pyrophosphate, trihydrate | Mn$_2$P$_2$O$_7$ · 3H$_2$O |
| manganese (II) sulfate | MnSO$_4$ |
| manganese (II) sulfate, dihydrate | MnSO$_4$ · 2H$_2$O |
| manganese (II) sulfate, heptahydrate | MnSO$_4$ · 7H$_2$O |
| manganese (II) sulfate, hexahydrate | MnSO$_4$ · 6H$_2$O |
| manganese (II) sulfate, monohydrate (natural szmikite) | MnSO$_4$ · H$_2$O |
| manganese (II) sulfate, pentahydrate | MnSO$_4$ · 5H$_2$O |
| manganese (II) sulfate, tetrahydrate | MnSO$_4$ · 4H$_2$O |
| manganese (II) sulfate, trihydrate | MnSO$_4$ · 3H$_2$O |
| nickel acetate | Ni(C$_2$H$_3$O$_2$)$_2$ |
| nickel carbonate | NiCO$_3$ |
| nickel carbonate, basic | 2NiCO$_3$ · 3Ni(OH)$_2$ · 4H$_2$O |
| nickel chloride | NiCl$_2$ |
| nickel chloride, hexahydrate | NiCl$_2$ · 6H$_2$O |
| nickel bromide | NiBr$_2$ |
| nickel bromide, trihydrate | NiBr$_2$ · 6H$_2$O |
| nickel formate, dihydrate | Ni(CHO$_2$)$_2$ · 2H$_2$O |
| nickel fluoride | NiF$_2$ |
| nickel (II) hydroxide | Ni(OH)$_2$ |
| nickel nitrate, hexahydrate | Ni(NO$_3$)$_2$ · 6H$_2$O |
| nickel nitrate | Ni(NO$_3$)$_2$ |
| nickel oxalate | NiC$_2$O$_4$ · 2H$_2$O |
| nickel orthophosphate | Ni$_3$(PO$_4$)$_2$ |
| nickel sulfate | NiSO$_4$ |
| nickel sulfate, heptahydrate (natural morensite) | NiSO$_4$ · 7H$_2$O |
| nickel sulfate, hexahydrate (single nickel salt) | NiSO$_4$ · 6H$_2$O |
| tin (II) chloride | SnCl$_2$ |
| tin (II) fluoride | SnF$_2$ |
| tin (II) orthophosphate | Sn$_3$(PO$_4$)$_2$ |
| tin (II) sulfate | SnSO$_4$ |
| tin (II) bromide | SnBr$_2$ |
| zinc bromide | ZnBr$_2$ |
| zinc acetate | Zn(C$_2$H$_3$O$_2$)$_2$ |
| zinc acetate, dihydrate | Zn(C$_2$H$_3$O$_2$)$_2$ · 2H$_2$O |
| zinc butyrate | Zn(C$_4$H$_7$O$_2$)$_2$ · 2H$_2$O |
| zinc chloride | ZnCl$_2$ |
| zinc fluoride | ZnF$_2$ |
| zinc formaldehyde, sulfoxylate | Zn(HSO$_2$ · CH$_2$O)$_2$ |
| zinc formate | Zn(CHO$_2$)$_2$ |
| zinc formate, hydrate | Zn(CHO$_2$)$_2$ · 2H$_2$O |
| zinc hydroxide | Zn(OH)$_2$ |
| zinc d-lactate | Zn(C$_3$H$_5$O$_3$)$_2$ · 2H$_2$O |
| zinc nitrate, trihydrate | Zn(NO$_3$)$_2$ · 3H$_2$O |
| zinc nitrate, hexahydrate | Zn(NO$_3$)$_2$ · 6H$_2$O |
| zinc oxalate | ZnC$_2$O$_4$ · 2H$_2$O |
| zinc oxide | ZnO |
| zinc orthophosphate | Zn$_3$(PO$_4$)$_2$ |
| zinc sulfate | ZnSO$_4$ |
| zinc sulfate (natural zinkosite) | ZnSO$_4$ |
| zinc sulfate, heptahydrate (natural goslarite) | ZnSO$_4$ · 7H$_2$O |
| zinc sulfate, hexahydrate | ZnSO$_4$ · 6H$_2$O |

1. Suitable Sequestered Metal Salts

The metal salts may have the metal ion chelated with other chelating agents, also called sequestering agents.

Examples of these chelating or sequestering agents are found in U.S. Pat. Nos. 2,828,182, 2,854,791, 2,906,762, 2,921,847, 2,943,100, 3,107,260, 3,051,563, 3,008,816, 2,961,311, 2,859,104, and 2,891,854. Other chelating and sequestering agents are described in "Chemistry of the Metal Chelate Compounds" by Martell and Calvin, published by Prentice Hall, Inc., 1952.

In using the metal ions which are sequestered with a sequestering agent or chelating agent it is important to adjust the particular sequestering agent with the particular metal ion in such a manner that it does not bind that particular metal ion so that the azide ion itself cannot form a complex metal azide salt composite described herein. This is achieved by balancing the factors mentioned by Martell and Calvin such as: the acid base properties of the chelate vs the acid base properties of the metal ion. For example, the metal ion of cobalt (II) is very easily chelated with many of the sequestering agents, whereas magnesium ion is not readily chelated so that the type and concentration of the chelating or sequestering agents used with magnesium is different from that used with cobalt.

The advantage of using the sequestering metal ion salts in the compositions described herein for applications to soil or plants is that not only is phytotoxicity of the azide reduced, but also the solubility of the particular metal ion may be increased so that a plant or a soil difficient in the metal ion such as cobalt or iron will have the benefits of both the azide ion and the benefit of the soluble form of the metal ion.

2. Suitable Azides

The azides used in these compositions are alkaline metal azides, and alkaline earth metal azides. Preferably, the azides are those which are stable and are non-explosive or which do not decompose in the presence of heat etc. Of these alkali earth metal azides and alkaline metal azides, the following are preferred:

| sodium azide | $NaN_3$ |
| potassium azide | $KN_3$ |
| rubidium azide | $RbN_3$ |
| barium azide | $Ba(N_3)_2$ |

The most preferred azides for these compositions are those of sodium azide and potassium azide or mixtures thereof.

3. Substances Not Present In The Compositions

In all embodiments of the invention, the compositions are substantially free from substance which decompose the azide. Examples of such substances are the metals copper, silver, lead, mercury, gold, and the ions of these particular metals, such as perchlorates, chlorates, iodides, etc., particularly iodides in the presence of bisulfite compounds which compounds when in the presence of the azide tend to decompose the azide. Consequently, during the preparation of the compositions of this invention care must be taken to avoid inclusion of these types of substances which have metal ions or anions that have a tendency in the presence of azide to cause decomposition.

In all embodiments of the invention, the compositions are prepared in such a manner as to avoid formation of molten azides together with metal oxides, or metals, which cause decomposition of azides, as described by Heinricht Egghart, in his article, "Decomposition of Potassium Azide Metals in the Presence of Metal Catalysts", *Inorganic Chemistry*, Vol. 2, 1963, pages 364–369.

4. Ratio Of Azide To Metal Salts In The Compositions

The compositions of this invention have a ratio of mole equivalents of azide ions from the azides used in the compositions to mole equivalents of the metal ions from the metal salts used in the composition within the range from 0.01 to 8, but generally it is from 0.1 to 4.0; preferably this ratio is within the range from 0.8 to 2.0, and especially useful is the range from 0.9 to 1.2

This ratio value of mole equivalents of azide ions to mole equivalents of the metal ions in the composition is calculated according to the following formulas:

$$\text{Ratio value} = \frac{\Sigma \text{ mole equivalent of azide ions in the composition}}{\Sigma \text{ mole equivalent of metal ions in the composition}}$$

$$\text{mole equivalent of azide ions} = \frac{\text{weight of an azide in the composition}}{\text{equivalent weight of the azide used in the composition}}$$

$$\text{equivalent weight of azide used in the composition} = \frac{\text{molecular weight of the azide used in the composition}}{\text{number of azide ions in the azide used in the composition}}$$

$$\text{mole equivalents of metal ion} = \frac{\text{weight of the metal salt in the composition}}{\text{equivalent weight of the metal salt in the composition}}$$

$$\text{equivalent weight of the metal salt in the composition} = \frac{\text{molecular weight of the metal salt}}{\text{total valence number of the metal ion in the metal salt}}$$

b. Probable Structure of the Compositions

For example, a composition containing 10.4 grams of sodium azide and 7.8 grams of ferrous chloride ($FeCl_2$) would have a ratio value of 1.3. A composition containing 10.4 grams of sodium azide, 10 grams of potassium azide, 8.4 grams of zinc chloride ($ZnCl_2$) and 5.85 grams of magnesium chloride ($MgCl_2$) has a ratio value of 1.15.

Without limiting the invention to the following explanation of the specific nature of some of the compositions contemplated herein, wherein the azide and metal salt are in chemical combination, it is believed that the azide is present at least in part in the form of a complex composite salt in which the metal ions of the metal salt (used in preparing the composition) are coordinated with one or more azide ions (provided from the azide) so as to form one or more ionic moieties represented by the general formula: $[Me_n^a(N_3)_x]^z$. In this formula Me represents a metal ion of the metal salt; e.g., zinc, magnesium, etc.; superscript a represents the specific charge of the metal ion; subscript n represents the number of metal ions; ($N_3$) represents the azide ion which coordinates with the metal ion; subscript x represents the number of azide ions coordinated with the metal ion; and superscript z represents the charge of the moiety. The chemical bond between the metal ion and the azide ion of the moiety is one which causes this moiety to act as if it were itself an ion, so as to form a complex composite salt of the general structure $[Me_n^a(N_3)_x]^z A_m B_r$. In this general structure, A represents the other portion of the azide used to form the composition; such as hydronium ion, sodium cation, potassium cation, calcium cation, magnesium cation, etc.; subscript m represents an integer which indicates the number of these cations of sodium found in the composition; B represents the anion of the metal salt used to form the composition; such as, the anions of chloride, phosphate, etc., the subscript r represents an integer which indicates the number of such anions of chloride, etc. found in the composition. In the composition there may be only one or there may be many different moieties present.

2. Embodiments Of The Composition a. Physical Mixtures Of Azide Granules And Metal Salt Granules One embodiment of this invention are solid compositions which encompass physical mixtures of azide granules and metal salt granules. These physical mixtures of azide granules and metal salt granules have the property of dissolving in a suitable solvent, such as water, to form a complex azide-metal salt composite, or which upon application to the soil or plant form a complex azide-metal salt composite described herein.

a 1. Amount Of Azide And Metal Salt Granules In The Mixtures

The amount of azide granules and metal salt granules in the physical mixture is such that when the composition dissolves in a suitable solvent, such as water, or is applied to the soil, or plant, the solution or the soil has therein, or the plant has thereon, an azide ion content and metal ion content in which the ratio of the mole equivalents of azide ion to mole equivalents of the metal ion from the metal salt in the solution, or the soil or upon the plant is within the ranges mentioned herein. This means that if the physical mixture of granules is applied to a region such as the soil or a plant and the region is wetted, for example, by rain, or by irrigation, then the granules dissolve within the water to form a solution in which the ratio of mole equivalents of azide ion to mole equivalents of metal ion is within the range mentioned herein thereby forming the metal ion and azide ion chemical combinations described herein. The solvent, such as water may originate from irrigation, or from rain, or from the soil itself, or it may be added to the granules to form a solution in situ for application to the plants or soil. The physical mixtures of the metal salts granules and azide granules consist of granules which have a range from 8 mesh to 200 mesh, preferably the range is from 10 mesh to 100 mesh. The mesh size of the particles of the physical mixture vary and depend upon the application; for example, larger sized mesh would be preferred when applying to the soil, whereas the smaller sized mesh would be preferred when the application of these mixtures are to the plants themselves, or if they are used to form a liquid composition in situ. In some cases it is preferred that the mixture be a heterogeneous one of different meshes so as to give a more even time release of the azide when applied to a plant, etc. than occurs with only the metal ion and azide ion chemical combinations described herein. The azide granules and metal salts granules may be prepared directly by precipitation from salt solutions. The metal salt granules or the azide granules or both may be treated by calcining, that is heating to higher temperature for a pre-determined time to form a more insoluble form so that during application the amount which dissolves in wet soil is decreased, thereby further extending the soil life of the compositions.

a 2. Other Materials Present In The Physical Mixtures

The physical mixtures may also contain a granule of a basic azide stabilized material so as to prevent the loss of azide through the occurrence of hydrolysis if exposed inadvertently to moist air. Examples of suitable basic materials are organic compounds such as amines, which may be incorporated upon or within the granules of the azide. Other basic stabilizing materials are, sodium hydroxide, potassium hydroxide, potassium carbonate, and sodium carbonate. These may be incorporated upon or within the azide granules of the azide, or may themselves be granules mixed with the azide granules and the metal salt granules. The preferred materials would be the potassium and the sodium carbonates. The amount of these materials may be from 0.1 percent to about 10 weight percent of azide in the mixture with the preferred range of 0.2 to 0.4 percent by weight of the azide in the mixture.

a 3. Preferred Metal Salts For The Physical Mixtures

The preferred metal salts for the physical mixture of azide granules and metal salt granules are the following:

| | |
|---|---|
| cobalt (II) chloride | $CoCl_2$ |
| cobalt (II) chloride, dihydrate | $CoCl_2 \cdot 2H_2O$ |
| coblat (II) chloride, hexahydrate | $CoCl_2 \cdot 6H_2O$ |
| cobalt (II) formate | $Co(CHO_2)_2 \cdot 2H_2O$ |
| coblat (II) nitrate | $Co(NO_3)_2 \cdot 6H_2O$ |
| cobalt (II) propionate | $Co(C_3H_5O_2)_2 \cdot 3H_2O$ |
| cobalt (II) sulfate | $CoSO_4 \cdot 7H_2O$ |
| cobalt (II) sulfate, heptahydrate (natural bieberite) | $CoSO_4 \cdot 7H_2O$ |
| cobalt (II) sulfate, monohydrate | $CoSO_4 \cdot H_2O$ |
| cobalt (II) bromide | $CoBr_2$ |
| cobalt (II) bromide, hexahydrate | $CoBr_2 \cdot 6H_2O$ |
| iron (II) carbonate | $FeCO_3$ |
| iron (II) chloride | $FeCl_2$ |
| iron (II) sulfate | $FeSO_4$ |
| magnesium acetate | $Mg(C_2H_3O_2)_2$ |
| magnesium acetate, tetrahydrate | $Mg(C_2H_3O_2)_2 \cdot 4H_2O$ |
| magnesium bromide | $MgBr_2$ |
| magnesium bromide, hexahydrate | $MgBr_2 \cdot 6H_2O$ |
| magnesium chloride | $MgCl_2$ |
| magnesium chloride, hexahydrate (natural bischorfite) | $MgCl_2 \cdot 6H_2O$ |
| magnesium nitrate, dihydrate | $Mg(NO_3)_2 \cdot 2H_2O$ |
| magnesium nitrate, hexahydrate | $Mg(NO_3)_2 \cdot 6H_2O$ |
| magnesium sulfate | $MgSO_4$ |
| magnesium sulfate, heptahydrate (Epon salt, natural epsomite) | $MgSO_4 \cdot 7H_2O$ |
| magnesium sulfate, monohydrate (natural kieserite) | $MgSO_4 \cdot H_2O$ |
| manganese (II) dibromide | $MnBr_2$ |
| manganese (II) dibromide, tetrahydrate | $MnBr_2 \cdot 4H_2O$ |
| manganese (II) dichloride (scacchite) | $MnCl_2$ |
| manganese (II) dichloride, tetrahydrate | $MnCl_2 \cdot 4H_2O$ |
| manganese (II) sulfate | $MnSO_4$ |
| manganese (II) sulfate, monohydrate | $MnSO_4 \cdot H_2O$ |
| manganese (II) sulfate, heptahydrate | $MnSO_4 \cdot 7H_2O$ |
| manganese (II) sulfate, pentahydrate | $MnSO_4 \cdot 5H_2O$ |
| manganese (II) sulfate, tetrahydrate | $MnSO_4 \cdot 4H_2O$ |
| nickel bromide | $NiBr_2$ |
| nickel bromide, trihydrate | $NiBr_2 \cdot 3H_2O$ |
| nickel chloride | $NiCl_2$ |
| nickel chloride, hexahydrate | $NiCl_2 \cdot 6H_2O$ |
| nickel nitrate, hexahydrate | $Ni(NO_3)_2 \cdot 6H_2O$ |
| nickel sulfate | $NiSO_4$ |
| nickel sulfate, heptahydrate (morensonite) | $NiSO_4 \cdot 7H_2O$ |
| nickel sulfate, hexahydrate (single nickel salt) | $NiSO_4 \cdot 6H_2O$ |
| tin (II) bromide | $SnBr_2$ |
| tin (II) chloride | $SnCl_2$ |
| tin (II) sulfate | $SnSO_4$ |
| zinc acetate | $Zn(C_2H_3O_2)_2$ |
| zinc acetate, dihydrate | $Zn(C_2H_3O_2)_2 \cdot 2H_2O$ |
| zince bromide | $ZnBr_2$ |
| zinc chloride | $ZnCl_2$ |
| zinc formate | $Zn(CHO)_2$ |
| zinc nitrate, trihydrate | $Zn(NO_3)_2 \cdot 3H_2O$ |
| zinc nitrate, hexahydrate | $Zn(NO_3)_2 \cdot 6H_2O$ |
| zinc sulfate, heptahydrate (natural gaslarite) | $ZnSO_4 \cdot 7H_2O$ |
| zinc sulfate, hexahydrate | $ZnSO_4 \cdot 6H_2O$ |

The metal salts especially preferred for the solid compositions of a physical mixture are: iron (II) chloride, iron (II) sulfate, iron (II) nitrate, iron (II) bromide, cobalt (II) chloride, cobalt (II) nitrate, cobalt (II) sulfate, cobalt (II) bromide, magnesium chloride, magnesium bromide, magnesium nitrate, magnesium sulfate, manganese (II) dibromide, manganese (II) dichloride, manganese (II) sulfate, nickel bromide, nickel chloride, nickel sulfate, nickel nitrate, tin (II) bromide, tin (II) chloride, tin (II) sulfate, zinc bromide, zinc chloride, zinc nitrate, zinc sulfate, and hydrates of these salts. The most preferred of these metal salts are the magnesium salts and zinc salts, particularly the anhydrous chlorides, nitrates, bromides, and sulfates.

b. Solid Compositions Of An Inert Material Impregnated With Metal Salt And Azide Another embodiment of this invention are solid compositions of an inert material; such as, clay, usually, in the form of granules which disintegrates within the soil within a few weeks to form materials in which plants may be grown or otherwise is disposed of in the soil without adverse effect upon plant life grown therein, impregnated with one or more metal salts and one or more azides. Preferably these impregnated granules also contain a basic azide stabilizing material of sodium hydroxide, potassium hydroxide, sodium carbonate, potassium carbonate, or mixtures thereof in the concentration ranges as described hereinbefore. These inert granules usually are of a mesh size from 10 to 80 mesh, preferably 16 to 30 mesh.

b 1. Types Of Inert Materials

Examples of suitable inert materials are: clays such as attapulgite clay, montmorillonite, kaolite, bentonite. Attapulgite clay is processed from the mineral attapulgite, a naturally sorptive clay mined only in southwestern Georgia and northwestern Florida, and is preferred. Various forms of the clay granules may be used, which forms are described in Engelhard Technical Bulletin, "Technical Information No. 151, - Agricultural Products for Pesticide Formulations". The "A", "AA", and "LVM" granules being preferred for soil application under irrigation conditions or extreme wetness.

b 2. Methods of Impregnation (1) Impregnation By Incorporationg The Azide And Metal Salt Into The Wet Inert Material Impregnation of these inert granules with both the azide and metal salt may be accomplished by different methods. One way is by incorporating the azide and a metal salt, or chelated metal salt into the clay while the clay is in a putty or mud-like, wet stage. This incorporation is preferably accomplished by using the metal salt in finely divided form having a mesh size from 200 to 50, generally from 200 to 100 and preferably from 200 to 150. This method of incorporating the metal salt or chelated metal salt into the mud-like clay is especially useful when the metal salts are slightly soluble metal salts, such as phosphates, oxides, etc., e.g., zinc phosphate, nickel oxide, etc. After thoroughly incorporating one or more azide salts, one or more metal salts, or one or more chelated metal salts, or a mixture thereof into the putty-like mass of clay, the entire clay mixture is then extruded or pelletized by means of an extrusion or pelletizer or other granular forming equipment. The product from the granular forming equipment is then calcined to a stable condition, for example, calcined in air at from 70° to 2000° Fahrenheit (20° to 1090° Centigrade), preferably from 100° to 500° Fahrenheit (38° to 260° Centigrade).

EXAMPLES I-X

Table 1 lists specific examples of solid compositions which may be formed by incorporating the azide and the metal salt into the inert material and calcining, that is heating at the desired temperature for a pre-determined time to change the granules into hard, easily handled materials which are resistant to attrition but which decompose within the soil. Column 1 gives the example number, column 2 gives the weight of attapulgite clay to be used, column 3 gives the weight of metal salt and the particular metal salt to be used, column 4 gives the weight of the azide and the particular azide to be used, column 5 gives the weight of water to be used, column 6 gives the calcining temperature and time to be used, and column 7 gives the ratio of mole equivalents of azide ion to mole equivalents of metal ion in the composition.

In these solid compositions in which azide ion is in combination with the metal salt any of the metal salts described herein, may be combined with azide ion within the ratios described herein. The source of the azide ion will vary depending upon the metal salt used for the composition. For example when the metal salt used is an oxide, hydroxide, or carbonate, then hydrazoic acid is not used as the source of azide ions. If the metal salt used is a chloride or bromide, or nitrate, then hydrazoic acid may be used as the source of azide ions.

TABLE 1

Solid Compositions - Inert granules impregnated with azide-metal salt by incorporating into wet clay.

| Example No. | Attapulgite (grams) | Metal Salt (grams) | | Azide (grams) | | Water (grams) | Calcining Temperature and Time (Fahrenheit) | (hours) | Azide/Metal Ion Ratio |
|---|---|---|---|---|---|---|---|---|---|
| I | 1000 | ZnO | (81) | $RbN_3$ | (127) | (300) | 500° F. | 1 hr. | 1.0 $Zn^{++}$ |
| II | 1000 | MgO | (40) | $NaN_3$ | (130) | (250) | 750° F. | 3 hr. | 1.0 $Mg^{++}$ |
| III | 1000 | $Fe_2O_3$ | (107) | $Ba(N_3)_2$ | (221) | (250) | 800° F. | 1 hr. | 0.5 $Fe^{++}$ |
| IV | 1000 | $Fe(OH)_2$ | (90) | $KN_3$ | (162) | (250) | 700° F. | 4 hr. | 1.0 $Fe^{++}$ |
| V | 1000 | $Al_2O_3$ | (34) | $KN_3$ | (162) | (300) | 600° F. | 1 hr. | 1.0 $Al^{+++}$ |
| VI | 1000 | $Co_3(PO_4)_2$ | (122) | $KN_3$ | (162) | (200) | 500° F. | 2 hr. | 1.0 + |
| VII | 1000 | $MgCO_3$ | (84) | $NaN_3$ | (130) | (200) | 400° F. | 5 hr. | 1.0 $Mg^{++}$ |
| VIII | 1000 | $Ni_3(PO_4)_2$ | (122) | $Ba(N_3)_2$ | (221) | (300) | 300° F. | 8 hr. | 1.0 $Ni^{++}$ |
| IX | 1000 | ZnO MgO | (40.7) (20) | $Ba(N_3)_2$ | (221) | (250) | 200° F. | 10 hr. | 1.0/$Zn^{++}$ + $Mg^{++}$ |
| X | 1000 | ZnO $Fe(OH)_2$ | (40.7) (45) | $NaN_3$ | (130) | (250) | 200° F. | 2 hr. | 1.0/$Zn^{++}$ + $Fe^{++}$ |

The preferred metal salts and azides are those described herein, with the magnesium and zinc metal salts being the most preferred as described hereinbefore, particularly the chlorides, nitrates, and sulfates.

(2) Impregnation By Wetting The Inert Material With Solutions Of Azide Or Metal Salt Or Both Azide And Metal Salt Another method of impregnating inert granules is to sprinkle a batch of inert granules such as 16/30 mesh ALVM grade attapulgite clay granules (Engelhard) with an aqueous or other solvent solution containing one or more azides, or containing both azides and a basic azide stabilizing material, described hereinbefore, such as sodium carbonate or potassium carbonate, until the surfaces of the granules appear uniformly wet. The granules are tumbled to obtain uniform wetting and absorption prior to the next addition of the solution. This wetting and tumbling is continued until the predetermined amount of azide to be impregnated within the granule is reached. The granules are sealed in a closed vessel for 2 or more hours at ambient temperature to equilibrate the moisture content of the granules. Then the granules are spread out in shallow trays and dried in air. The temperature of air may vary from 68° to 500° F. (20°–260° Centigrade).

After drying, the azide impregnated granules are then impregnated with one or more metal salts, by sprinkling with an aqueous solution of the metal salt or salts, and tumbling as described above until a pre-determined amount of the metal salt or salts are added. The granules are equilibrated for moisture content, then dried.

As an alternative of this method, the granules can be impregnated with an aqueous solution containing both azides and metal salts, or with solutions containing azide, metal salts, and a basic azide stabilizing material. Any method of wetting the inert granules may be used such as sprinkling or spraying. The granules may be dipped into the solutions, the excess solution drained, and the granules are dried. Other well known techniques for impregnation may be used.

Impregnation may be carried out at temperatures from 2° to 100° Centigrade, preferably from 15° to 70° Centigrade. Drying may be accomplished by any known method such as vacuum drying, but preferably air drying is used.

Inert granules impregnated by means of solutions may be dried at temperatures as high as 500° Fahrenheit (F.) (260° Centigrade) in dry air and then gradually equilibrated with cool moist air until the granule is in equilibrium with air which has a relative humidity from 10 to 99 percent. Generally the drying range is from ambient to 200° Fahrenheit (93.2° Centigrade), preferably from 70° to 150° Fahrenheit (21° to 65.5° Centigrade). The humidity of the dry air is generally from 10 to 99 percent, normally from 15 to 70 percent, and preferably from 25 to 50 percent. The preferred equilibrating conditions for the impregnated granules is 70° to 90° Fahrenheit (21° to 32° Centigrade), at a relative humidity from 50 to 60 percent.

The inert granules can be impregnated with all of the azides and metal salts mentioned hereinbefore and/or with the metal salts which have the metal ion sequestered or chelated with other chelating agents, previously mentioned herein.

The total amount of azide salt together with metal salt within the inert granules may vary from 1 to 50 weight percent, but generally varies from 2 to 15 weight percent, with the range of 5 to 10 weight percent being preferred.

When impregnating inert granules, best results are obtained with water soluble metal salts; particularly magnesium or zinc water soluble salts. Magnesium nitrate, magnesium chloride, magnesium sulfate, zinc nitrate, zinc chloride, zinc sulfate, or mixtures of these salts are especially preferred. The metal salt used will vary with the particular use for which the compositions are prepared. For agricultural formulations, it will depend on the particular disease and with the toxicity level of the plant to the metal; for example, a magnesium salt may be used together with a zinc salt in ratios of 0.1 to 100 parts by weight of magnesium to zinc. In some cases, one metal salt may be used in trace amounts to control plant pests which are very sensitive to trace amounts of metal.

EXAMPLES XI–XXII

Specific examples of inert granules impregnated by wetting are shown in Table 2. Column 1 of Table 2 gives the example number, column 2 gives the initial weight percent based on the weight of the dry granules prior to impregnation with azide or basic azide stabilizer or metal salt prior to impregnating with the metal salt, column 3 gives the initial weight percent based on the weight of the dry granules prior to impregnation with azide or the basic azide stabilizer or metal salt and the basic azide stabilizer within the granule, column 4 gives the weight and type of metal salt and weight of water used to impregnate a 100 gram batch of granules impregnated with azide, column 5 gives the type of inert granule and mesh size, and column 6 gives the ratio of the number of azide ions to unit charge of metal ion.

Procedure

The granules set forth in Table 2 were impregnated with the specified azide and metal salt by the following procedure:

A batch of the inert granules, for example a (3.62 kilograms) 16/30 mesh ALVM grade attapulgite clay granules (Engelhard), were sprinkled with a solution containing 385 grams of sodium azide (98% $NaN_3$), 90 grams of potassium carbonate (99% $K_2CO_3$), and 120 grams of water at ambient temperature. A portion of the solution was sprinkled on the granules until the surfaces appeared to be uniformly wet. The granules were then tumbled with a rake to obtain uniform wetting and absorption prior to addition of another portion of the solution. The addition of the solution and tumbling of the granules was continued until all of the solution was added. The temperature during impregnation was ambient. The granules were sealed in a closed container at ambient temperature for 2 hours to equilibrate the moisture content of the granules and spread out in shallow trays and dried in air which was at 90° Fahrenheit. This gave granules having 10.4 weight percent sodium azide and 2.4 weight percent potassium carbonate.

Portions of these azide impregnated granules were then impregnated with various metal salts according to the following impregnation procedures.

One hundred (100) grams of the dried azide impregnated granules were placed in a 3 inch deep, 4.5 inch diameter jar. About 1.5 cubic centimeters (cc) of a solution of metal salt are added dropwise (20–25 drops) while the jar was rotated so as to cause each drop to contact a fresh portion of the granules. Then the jar of granules was rotated and shaken to cause uniform wetting of the granules. The procedure was repeated with another 1.5 cc of solution, until all of the impregnating solution was used up. Then the jar was rotated and shaken for about 15 to 20 minutes to effect complete, uniform impregnation. The impregnation was conducted at ambient temperature. The granules were removed from the jar and spread upon a flat, plastic sheet and dried for about 2 hours in direct sunlight and in air which had a temperature of 90° F. During this impregnation some azide is lost from the granule.

In impregnating granules by wetting, it is preferred that the impregnation with azide be accomplished first, and preferably with azide and a basic azide stabilizing material, followed by drying, before impregnating with a metal salt. It is preferred that the metal salt solution be at a pH from 4 to 10, preferably from 6 to 8.

composition described herein, or for coating the inert materials mentioned herein, so as to form granules of an

TABLE 2

AZIDE-METAL SALT IMPREGNATED GRANULES

| Example No. (Granule No.) | Initial Azide Weight % | Other Salt Weight % | Metal Salt Weight per 100 grams of granules Water (grams) | Granule Type and Mesh | Azide/Metal Ion Ratio |
|---|---|---|---|---|---|
| XI | NaN$_3$ 10.4% | K$_2$CO$_3$ 2.4% | FeCl$_2$ (7.8 grams) in 15 grams of water | Attapulgite ALVM 16/30 mesh (Engelhard) | N$_3^-$/Fe$^{2+}$ ≈ 1.3 |
| XII | NaN$_3$ 10.4% | K$_2$Co$_3$ 2.4% | FeCl$_3$ 6H$_2$O (11.1 grams) in 15 grams of water | Attapulgite ALVM 16/30 mesh (Engelhard) | N$_3^-$/Fe$^{3+}$ ≈ 1.3 |
| XIII | NaN$_3$ 10.4% | K$_2$CO$_3$ 2.4% | MnCl$_2$ (7.8 grams) in 15 grams of water | Attapulgite ALVM 16/30 mesh (Engelhard) | N$_3^-$/Mn$^{2+}$ ≈ 1.3 |
| XIV | NaN$_3$ 10.4% | K$_2$CO$_3$ 2.4% | ZnCl$_2$ (8.4 grams) in 15 grams of water | Attapulgite ALVM 16/30 mesh (Engelhard) | N$_3^-$/Zn$^{2+}$ ≈ 1.3 |
| XV | NaN$_3$ 10.4% | K$_2$CO$_3$ 2.4% | Second impregnation in 15 grams of water only | Attapulgite ALVM 16/30 mesh (Engelhard) | N$_3^-$/Me = ∞ |
| XVI | NaN$_3$ 10.4% | K$_2$CO$_3$ 2.4% | MgCl$_2$ (5.85 grams) in 15 grams of water | Attapulgite (AARVM) 18/35 mesh (Engelhard) | N$_3^-$/Mg$^{2+}$ ≈ 1.3 |
| XVII | KN$_3$ 10% | K$_2$CO$_3$ 2% | Mg(NO$_3$)$_2$ . 6H$_2$O (7.9 grams) in 15 grams of water | Attapulgite ALVM 8/15 mesh (Engelhard) | N$_3$/Mg$^{2+}$ ≈ 2.0 |
| XVIII | KN$_3$ 10% | K$_2$CO$_3$ 2% | Zinc ethylenediamine tetraacetate dihydrate (Sequestrene$^{(R)}$ zinc Geigy Chemical Co.) (10 grams) in 15 grams of water | Montmorillonite 8/16 mesh | N$_3^-$/Zn$^{2+}$ ≈ 2.8 |
| XIX | KN$_3$ 10% | K$_2$CO$_3$ 2% | Zinc ethylenediamine tetraacetate dihydrate (Sequestrene$^{(R)}$ zinc Geigy Chemical Co.) (10 grams) in 15 grams of water impregnated twice with the zinc solution | Montmorillonite 8/16 mesh | N$_3^-$/Zn$^{2+}$ ≈ 1.4 |
| XX | RbN$_3$ 10% | K$_2$CO$_3$ 12% | Al(NO$_3$)$_3$ . 9H$_2$O (10 grams) in 15 grams of water | Montmorillonite 8/100 mesh | N$_3^-$/Al$^{3+}$ ≈ 0.99 |
| XXI | NaN$_3$ 10.4% | K$_2$CO$_3$ 2% | Technical sodium ferric diethylenetriamine pentaacetate iron (Sequestrene$^{(R)}$ green foliage stimulant - Geigy) in 25 grams of water impregnated twice | Attapulgite (AVLM) 8/50 mesh | N$_3$/Fe$^{3+}$ ≈ 5.0 |
| XXII | NaN$_3$ 10.4% | K$_2$CO$_3$ 2% | MgCl$_2$ (6.0 grams) in 15 grams of water | Attapulgite (AVLM) 16/30 mesh | N$_3^-$/Mg$^{2+}$ ≈ 1.26 | c. Precipitated Solid Azide-Metal Salt Compositions

Another embodiment of the invention are precipitated solid azide-metal salt composites in which one or more azides and one or more metal salts are combined by dissolving the azides and metal salts in a suitable solvent such as water, ammonia, water ammonia mixtures, water-ethanol mixtures, and causing the precipitation of the azide-metal salt composite by any of the known precipitation techniques. For example the solvent may be evaporated to the point where the remaining solvent is super saturated, and the super saturated solution may be rapidly cooled, or seeded to cause precipitation of the azide-metal salt composite.

Alternatively the azides and metal salts mentioned hereinbefore could be dissolved in a warmed solvent to the point of saturation, and then the solvent is rapidly evaporated, for example under vacuum so as to cause precipitation of the azide-metal salt composite.

The precipitated azide-metal salt composite may be further dried, and then ground into a powder for direct application to soils or plants, or for forming the liquid inert material impregnated with the azide-metal salt composite mentioned herein.

The preferred azides are those mentioned hereinbefore, especially sodium and potassium azides and mixtures thereof, and the preferred metal salts are the more soluble metal salts mentioned hereinbefore, especially those of magnesium and zinc.

These precipitated azide-metal salt composites preferably will include a basic azide stabilizing material, preferably sodium hydroxide, potassium hydroxide, potassium carbonate, and sodium carbonate, or mixtures thereof, in the concentration ranges mentioned herein.

During formation of these precipitated azide-metal salt composites care is taken to insure that they are substantially free from substances mentioned herein which cause decomposition of the azide.

d. Granules Of Particles Of Azide Metal Salt Having A Low Tendency To Form Dust (1) Description Of The Granules Another embodiment of this invention are granules which contain particles of one or more metal salts described hereinbefore which are partly in combination with and physically in contact with particles of one or more azides described hereinbefore. These particles of the metal salts and azides are bonded together to form granules substantially free from angular surfaces and from 100 to 6 mesh in size, and having a low tendency to form dust and a good resistance to attrition. Preferably, they also contain a basic azide stabilizing material described hereinbefore. Generally these granules also contain particles of an inert carrier or diluent such as potassium chloride, potassium bromide, sodium chloride, and sodium bromide.

Preferably, these granules comprise particles of azide, particularly sodium azide or potassium azide or both, and particles of anhydrous chlorides, nitrates, and sulfates, of the metal ions of iron (II), iron (III), cobalt (II), nickel, zinc, magnesium, manganese (II), aluminum, and tin (II). Metal salts especially preferred for these granules are the anhydrous chlorides, sulfates, and nitrates of zinc and magnesium. The particles of azide and metal salt are bonded together to form a granule which has an appearance similar to crystals of the Botryoidal system, that is the granule looks like a compact bunch of grapes, with the small round particles of the azide and metal salt being the grapes, which particles are smoothly bonded to each other to form a granule of uniform size and shape. The bonding between the particles may result from the chemical composition formed during processing through the wetting of the surfaces of the particles, causing dissolving of azide and metal salt to form a solution which coats the outer surfaces of the particles to form a binder which binds the particles together. Preferably this binder contains a binder material such as dextrin, polyvinyl alcohol, alkali metal silicates or alkaline earth metal silicates.

The preferred binder material is potassium silicate, sodium silicate or mixtures thereof applied as an aqueous solution during formation of the granules. The weight percent of binder material may vary from 0.2 weight percent to 10 weight percent of the dry granule, with the balance being an azide or mixtures of azides and one or more metal salts mentioned hereinbefore. In these granules the weight ratio of azide to metal salt is adjusted to provide for an azide ion to unit charge of metal ion ratio within the limits hereinbefore mentioned. It is preferred that these granules further comprise solid particles of a diluent of alkali metal halides, with sodium chloride, potassium chloride, sodium bromide, potassium bromide, or mixtures thereof being preferred. These particles are intermixed with and in contact with the other component particles of the granule.

It is preferred that these granules further comprise particles of an azide-stabilizing basic material salt mentioned herein. Preferred salts of sodium carbonate, potassium carbonate, potassium hydroxide, sodium hydroxide, or mixtures of these salts.

In these granules containing particles of an azide and particles of a metal salt, the particles comprising the granules varies in size from 200 mesh to 100 mesh (0.075 millimeters to 0.150 millimeters), and the granule itself varies from 100 mesh to 6 mesh (0.150 millimeters to 2.36 millimeters). The granules have a low tendency to form dust and a good resistance to attrition as evidenced by a friability value of less than 5 percent. The friability value is determined by the standard method described in "Determination of Hardness of Granular Fullers Earth and Bauxite," *Standard Methods* 311, Engelhard Minerals and Chemical Corp., Menlo Park, Edison, New Jersey. The method is also described by W. Van Valkenburg, *Pesticide Formulation Manual*, Dekor, Inc., New York, N.Y. (1973) page 158.

EXAMPLE XXIII

Procedure

These granules by way of example would be formed as follows. A blend of sodium azide ($NaN_3$) particles and 0.75 weight percent of ground silica particles (an anticaking agent) are air milled to form finely divided particles (95 percent minus 200 mesh, 0.075 millimeters in diameter). Finely divided particles of potassium chloride (KCl) (100 percent minus 100 mesh, 50 percent minus 200 mesh), and potassium carbonate ($K_2CO_3$), (100 percent minus 100 mesh, 50 percent minus 200 mesh) are also similarly prepared, as well as finely divided particles of anhydrous zinc chloride ($ZnCl_2$) (100 percent minus 100 mesh, 50 percent minus 200 mesh). A mixer is charged with 35 parts by weight of this sodium azide, 45 parts by weight of the zinc chloride particles, 15 parts by weight of potassium chloride particles, and 3 parts by weight of the potassium carbonate particles, and operated for 5 minutes to produce a thoroughly mixed blend of the dry particles.

(2) Amount Of Ingredients Present In The Granules

An aqueous solution of sodium silicate (binder material) is prepared by diluting with tap water (1:1 by volume) a sodium silicate solution containing 19.52 weight percent of silicon dioxide and 6.52 percent by weight of sodium oxide.

A pan-granulator is used which has a rotatable pan granulation pan with a diameter of 16 inches, and a lip height of 1.5 inches. Three plows are positioned above the rotatable pan with the bottom of each plow about ⅜ inch from the pan surface. The position of these plows when viewed from above the rotating pan are as follows. The first plow, 3¾ inches long, is located in the 12 o'clock position, a distance of 1.5 inches from the center of the pan to the center of the plow, with the length of its blade running from top (12 o'clock position) to the bottom (6 o'clock position). The second plow, 4⅝ inches long, is at the 1 o'clock position, a distance of 5.5 inches from the pan center to plow center; its blade length running from the top (12 o'clock position) to the bottom (6 o'clock position) of the pan. The third plow, 2 inches long, is at the 2 o'clock position, a distance of 7 inches from the center of pan to the center of the plow, and its blade is running from top to bottom.

The pan is rotated clockwise at 33 revolutions per minute about an axis set at 50 degrees from the horizontal, as measured vertically from the 6 o'clock position of a horizontal line (viewed from above, running from the 6 o'clock position to the 12 o'clock position).

The blend of dry components is applied to the rotating pan through a vibrating screw feeder at a rate of 345 grams per minute. The delivery nozzle of the screw feeder is located at the 3 o'clock position, 4.5 inches from the center of the pan and 1 inch above the surface of the pan.

The binder material (specific gravity 1.128) is supplied to the pan at a rate of 61 cubic centimeters per minute through a spray nozzle (T Jet X-1, 40 pounds per inch of pressure). The spray nozzle is located at the 3 o'clock position, 2 inches above the surface of the pan and 1.5 inches from center of the pan.

Under these pan granulating conditions, 400 grams of granules per minute are produced. These granules are collected within a tray and air dried at 205 degrees Fahrenheit for about 16 hours, during which time they lose about 12.7 weight percent of moisture. The particle size of the granules are as follows:

8.98 weight percent were from 8 to 6 mesh,
4.52 weight percent were from 10 to 18 mesh,
33.13 weight percent were from 12 to 10 mesh,
44.19 weight percent were from 24 to 12 mesh,
3.17 weight percent were from 28 to 24 mesh, and
6.00 weight percent were from 40 to 100 mesh.

The friability value of the granules are 4.5 percent when determined by the standard method in which 50 grams of the granules of 10 to 12 mesh size are placed in a sieve pan together with 15 steel balls of ⅜ inch diameter. The sieve pan is oscillated for 10 minutes on a mechanical shaker. The weight percent of the granules which degraded to a particle size of less than 60 mesh is determined, as less than 5 percent.

This low value of friability of less than 5 percent is evidence of the low tendency of the granules to form dust by attrition of the granules during loading, shipping, handling, and use.

These granules containing particles of an azide and particles of a metal salt may have various proportions of the different ingredients as well as various proportions of different size particles of the ingredients. These variations will be in accordance with the particular use of the granular compositions.

The content of the azide in the granule may vary from 20 to 60 weight percent. Generally, the azide will be from 30 to 50 weight percent, but preferably it is from 35 to 45 weight percent, with a range from 45 to 55 weight percent being especially preferred.

The content of the metal salt in the granule is adjusted to being within the ratio limits hereinbefore mentioned for the ratio of the mole equivalents of azide ions to the mole equivalents of metal ion in the composition.

The content of the diluent if used will be from 1 weight percent to 25 weight percent, but generally it will be from 10 weight percent to 20 weight percent but preferably it is from 12 to 15 weight percent.

The content of the basic azide stabilizing material is, generally from 0.5 to 10 weight percent of the azide in the composition, but preferably it is from 1 to 5 weight percent, with a range from 2 to 4 percent being especially preferred. Sodium hydroxide, potassium hydroxide, sodium carbonate, potassium carbonate, or mixtures thereof are the preferred basic azide stabilizer material.

The content of the binder material is generally from 0.1 to 10 weight percent, but preferably from 0.2 to 10 weight percent, with a range from 1 to 3 weight being especially preferred.

The size of the particles of the ingredients or materials comprising the granules will generally vary from 270 mesh to 80 mesh, preferably from 230 mesh to 100 mesh, with the range from 200 mesh to 100 mesh being especially preferred.

The granules containing particles of azide and particles of a metal salt may be made by other methods, such as by disc granulation, or by the process disclosed in U.S. Pat. No. 3,711,254.

e. Liquid Compositions of Metal Salts And Azide (1) Description Of The Liquid Compositions Another embodiment of this invention are liquid compositions in which the metal salts and azide are dissolved within a solvent compatible with the metal salts and azide which dissolves those materials. The liquid compositions contain from 200 parts per million of azide ion to the maximum amount dissolved within the particular solvent. The solvents which may be used are water, alcohol, such as methanol, ethanol, mixtures of water and these alcohols, or mixtures of water, alcohol, and an emulsifiable agent. Water is the preferred solvent.

The liquid compositions are preferably formed from hydrazoic acid, sodium azide, potassium azide, or mixtures thereof, and one or more of the metal salts which are soluble in water. The preferred soluble metal salts are those chlorides, nitrates, bromides, and sulfates mentioned hereinbefore.

These liquid compositions may also contain the chelating or sequestering agents mentioned herein.

The general range of the ratio of the mole equivalents of azide ions to mole equivalents of metal ion in these liquid compositions is from 0.1 to 4.0; the preferred range is from 0.8 to 2.0; and especially preferred is the range from 0.9 to 1.2.

Preparation Of The Liquid Compositions

Liquid compositions are provided in any of various ways. According to one preparation, a pre-determined amount of a metal salt or salts such as $ZnCl_2$ is dissolved in a pre-determined amount of a solvent in which the azide and metal salt is soluble, e.g., water, followed by the dissolving of a pre-determined amount of azide in the resulting aqueous composition. Alternatively, an aqueous solution of the azide may be mixed with an aqueous solution of the metal salt. For example, an aqueous solution of 200 grams of water containing 20 grams of zinc nitrate, $Zn(NO_3)_2$, may be mixed with 780 grams of an aqueous solution containing 20 grams of potassium azide, $KN_3$, to form 1000 grams of a liquid composition containing 20 grams of $Zn(NO_3)_2$, 20 grams of $KN_3$, and 960 grams of water, $H_2O$.

Another procedure is to form in situ the sodium azide or like azide solution by mixing an aqueous solution of hydrazoic acid, also called azoimide, ($HN_3$), with an aqueous solution of sodium hydroxide.

Another procedure is to form in situ the soluble metal salt, such as magnesium chloride, or nitrate by dissolving in an acid solution such as hydrochloric acid, the metal itself or an insoluble salt of the metal such as oxide, carbonate, or hydroxide. Alternatively, the solutions of metal salts may be formed by electrolysis.

The temperature of the liquid composition during formation may be from 2° C. to 100° C., preferably it is about 20° C.

EXAMPLES XXIV-XXXVIII

The following examples illustrate the manner in which this invention may be practiced:

The following liquid compositions were prepared by mixing an aqueous solution containing a single metal salt with an aqueous solution containing only potassium azide and diluting the resulting solution with distilled water to the proper concentration.

Table 3 lists the specific liquid compositions of azide-metal salt, formed by mixing the following solutions and diluting with water. The solutions were prepared by dissolving a pre-determined amount of the salt in 100 cubic centimeters (cc) of water at room temperature:

Solution A - 0.63 grams of manganese (II) chloride ($MnCl_2$) in 100 cc of water.
Solution B - 0.68 grams of zinc chloride ($ZnCl_2$) in 100 cc of water.

Solution C - 0.63 grams of ferrous chloride ($FeCl_2$) in 100 cc of water.

Solution D - 0.81 grams of potassium azide ($KN_3$) in 100 cc of water.

Column 1 of Table 3 gives the example number, column 2 gives the amount of azide solution used in cubic centimeters (cc), column 3 gives the amount of metal salt solution used, and the particular solution used, column 4 gives the amount of distilled water added, column 5 gives the weight of $KN_3$ in the composition, column 6 gives the weight of the metal salt in the composition, column 7 gives azide to unit charge of metal ion ratio in the composition, and column 8 gives the weight of azide ion in the liquid composition in parts per million, ppm.

f. Slurry Compositions of Metal Salts and Azides

Another form of the liquid compositions of this invention are slurries, which contain a liquid phase with the metal salt and azide dissolved therein, and a solid phase containing the metal salt and azide. The solid phase being in equilibrium with the liquid phase. These types of liquid compositions are useful for transporting the liquid composition and are in such a form that they may be easily diluted with the solvent or other solvents mentioned hereinbefore at the place of use so as to form liquid compositions having the desired range of azide ions.

which allows applying azide ion to plants which may be sensitive to azide ion in the range where fungi, bacteria, and other plant pests are controlled, without permanently harming the plants. The solid compositions are less phytotoxic to plants sensitive to azide ions, are resistant to disintegration under irrigation conditions, and have a slower release rate of azide ion, whereby the soil persistency of the azide ion is extended and/or the amount of azide ion within the soil, or on the plant is relatively constant under different conditions of wetness. Some of the compositions also increase the growth of beneficial soil micro-flora such as *Trichoderma viride* which are natural biological control agents.

PHYTOTOXICITY

EXAMPLES XXXIX-XLII

The following examples listed in Table 4 illustrate the reduced phytotoxicity of the liquid compositions. In these examples, cucumber plants which were grown to the stage where the vines were from 18 to 24 inches in length, were sprayed to the dripping point with the liquid composition, and observations were made for damage to the plants for one week.

Column 1 of Table 4 lists the example number, column 2 gives the liquid composition of Table 3 (example number) sprayed on the plant, column 3 gives the parts per million (ppm) (weight) of azide in the solution,

TABLE 3

| Example No. (Liquid Composition) (No.) | Amount of Azide Solution (Solution D) | Amount of Metal Solution (Solution A, B, or C) | Water Centimeters (cc) | Composition Grams of $KN_3$ | Grams of salt | Azide/Metal Ratio | | ppm - $N_3$ by weight |
|---|---|---|---|---|---|---|---|---|
| XXIV | 5 cc | 5 cc A | 90 cc | .040 | 0.0315 | 1.0 | $N_3^-/Mn^{++}$ | 200 |
| XXV | 10 cc | 10 cc A | 80 cc | .081 | 0.0630 | 1.0 | $N_3^-/Mn^{++}$ | 400 |
| XXVI | 15 cc | 15 cc A | 70 cc | .121 | 0.0945 | 1.0 | $N_3^-/Mn^{++}$ | 600 |
| XXVII | 25 cc | 25 cc A | 50 cc | .202 | 0.1575 | 1.0 | $N_3^-/Mn^{++}$ | 1000 |
| XXVIII | 40 cc | 40 cc A | 20 cc | .324 | 0.252 | 1.0 | $N_3^-/Mn^{++}$ | 1600 |
| XXIX | 5 cc | 5 cc B | 90 cc | .040 | 0.034 | 1.0 | $N_3^-/Zn^{++}$ | 200 |
| XXX | 10 cc | 10 cc B | 80 cc | .081 | 0.068 | 1.0 | $N_3^-/Zn^{++}$ | 400 |
| XXXI | 15 cc | 15 cc B | 70 cc | .121 | 0.102 | 1.0 | $N_3^-/ZN^{++}$ | 600 |
| XXXII | 25 cc | 25 cc B | 50 cc | .202 | 0.170 | 1.0 | $N_3^-/ZN^{++}$ | 1000 |
| XXXIII | 40 cc | 40 cc B | 20 cc | .324 | 0.272 | 1.0 | $N_3^-/Zn^{++}$ | 1600 |
| XXXIV | 5 cc | 5 cc C | 90 cc | .040 | 0.0315 | 1.0 | $N_3^-/Fe^{++}$ | 200 |
| XXXV | 10 cc | 10 cc C | 80 cc | .081 | 0.0630 | 1.0 | $N_3^-/Fe^{++}$ | 400 |
| XXXVI | 15 cc | 15 cc C | 70 cc | .121 | 0.0945 | 1.0 | $N_3^-/Fe^{++}$ | 600 |
| XXXVII | 25 cc | 25 cc C | 50 cc | .202 | 0.1575 | 1.0 | $N_3^-/Fe^{++}$ | 1000 |
| XXXVIII | 40 cc | 40 cc C | 20 cc | .324 | 0.252 | 1.0 | $N_3^-/Fe^{++}$ | 1600 |

PROPERTIES AND APPLICATIONS OF THE COMPOSITIONS

The compositions of this invention exhibit useful agricultural properties such as reduced phytotoxicity column 4 gives the mole equivalents of azide ion to mole equivalents of metal ion ratio, and column 5 gives the experimental results.

TABLE 4

PHYTOTOXICITY TESTS OF LIQUID COMPOSITIONS

| Example No. | Liquid Composition (From Table 3) | ppm (weight) (Azide ion $N_3^-$) | $N_3^-/Me^+$ Ratio | Results |
|---|---|---|---|---|
| XXIX | XXXVII | 1000 | $N_3^-/Fe^{++} \approx 1.0$ | A marginal leaf burn within 24 hours from which the plant recovered within one (1) week. |
| XL | XXXII | 1000 | $N_3^-/Zn^{2+} \approx 1.0$ | A marginal leaf burn within 24 hours from which the plant recovered within one (1) week. |
| XLI | * | 1000 | No metal | Severe leaf burn within 24 hours with no recovery for the plant within one (1) week. |
| XLII | ** | 200 | No metal | A marginal leaf burn within 24 hours from which the plant recovered within one (1) week. |

*Solution prepared by dissolving 0.202 grams of $KN_3$ (potassium azide) in 100 cubic centimeters of distilled water.
**Solution prepared by dissolving 0.040 grams of $KN_3$ (potassium azide) in 100 cubic centimeters of distilled water.

The following examples in Table 5 illustrate the reduced phytotoxicity of granules on plants sensitive to azide ions impregnated with the azide-metal salt by wetting.

EXAMPLES XLIII-XLVI

PHYTOTOXICITY TEST PROCEDURE

A batch of potting soil (15 pounds, 6.8 kilograms) was mixed with 15 grams of the specified impregnated inert granules (from Table 2) in a rotary blender and the moisture of the soil mixture was adjusted to good germination level. The soil mixture was placed in a greenhouse flat for one week, and then seeded with a first row of 50 radish seeds, and one week later reseeded with a second parallel row of 50 radish seeds. Visual observations were made of their growth and a final observation was made 18 days after the first row was planted and 11 days after the second row was planted.

Column 1 of Table 5 gives the example number, column 2 gives the granule number (Example number) of the impregnated granules (Table 3), column 3 gives the weight percent of the azide, column 4 gives the metal salt and its weight percent, column 5 gives the ratio of the number of azide ions per unit charge of metal ion, column 6 gives the percent germination of radish seeds in the first row, and the average height of the plants in inches, and column 7 gives the percent germination of the radish seeds in the second row and the average height of the plants.

liters of a standard ferric nitrate solution (2 grams of hydrated ferric nitrate ($Fe(NO_3)_3 \cdot 6H_2O$), 5 milliliters of concentrated nitric acid ($HNO_3$), diluted to one liter with deionized water).

The intensity of the red color formed by the reaction of azide with ferric nitrate was measured colorimetrically. The colormetric value was compared to those of standard solutions, and the percentage of azide ion released was calculated from these colormetric values.

Column 1 of Table 6 gives the example number, column 2 gives the granule number (Example number from Table 3), column 4 gives the weight percent of azide, column 5 gives the metal salt and its weight percent, and column 6 gives the ratio value of the mole equivalents of azide ions to the mole equivalents of metal ions in the composition.

TABLE 6

| | | RELEASE RATE OF AZIDE IONS | | | |
|---|---|---|---|---|---|
| Example No. | Granule No. | Initial Azide Weight Percent | Metal Salt Weight Percent | $N_3^-$/Metal Ion Ratio | % Azide Ion Released |
| XLVII | * | $NaN_3$, 10.4% | 0 | | 35.4 |
| XLVIII | XI | $NaN_3$, 10.4% | ($FeCl_2$), 7.8% | $N_3^-/Fe^{2+} \approx 1.3$ | 20.7 |
| XLIX | XII | $NaN_3$, 10.4% | ($FeCl_3 \cdot 6H_2O$), 11.1% | $N_3^-/Fe^{3+} \approx 1.3$ | 17.2 |
| L | XIII | $NaN_3$, 10.4% | ($MnCl_2$), 7.8% | $N_3^-/Mn^{2+} \approx 1.3$ | 19.6 |
| LI | XIV | $NaN_3$, 10.4% | ($ZnCl_2$), 8.9% | $N_3^-/Zn^{2+} \approx 1.3$ | 15.1 |

* Granules from Example XLIV from Table 5

RESISTANCE OF SOLID COMPOSITIONS TO DISINTEGRATION

EXAMPLES LII-LVII

The following examples illustrate the resistance to disintegration by solid compositions of inert granules impregnated with azidemetal salt compositions. The test procedure simulated irrigation conditions which occur in the field.

Test Procedure for Disintegration

A one gram batch of the impregnated granules was placed upon a buchner funnel (size - inner diameter 10.2

TABLE 5

| | | PHYTOTOXICITY OF INERT GRANULES IMPREGNATED WITH AZIDE-METAL SALT BY WETTING | | | | |
|---|---|---|---|---|---|---|
| Example No. | Granule No. | Initial Azide Weight Percent | Metal Salt Weight Percent | Ratio of $N_3^-$/Metal Ion | % Of Germination And Ave. Plant Height (in.) Of First Row | % Of Germination And Ave. Plant Height (in.) Of Second Row |
| XLIII | * | 0 | 0 | 0 | 100%, 3 in. | 100%, 2 in. |
| XLIV | ** | $NaN_3$ - 10.4% | 0 | | 2%, 3/16 in. | 8%, 3/4 in. |
| XLV | XIV | $NaN_3$ - 10.4% | $ZnCl_2$ - 8.4% | $N_3^-/Zn^{2+} \approx 0.8$ | 70%, 1 1/4 in. | 70%, 2 in. |
| XLVI | XVI | $NaN_3$ - 10.4% | $MgCl_2$ - 6% | $N_3^-/Mg^{2+} \approx 1.0$ | 54%, 1 in. | 84%, 1 in. |

*Granules - without azide-metal salt
**The granules were formed by impregnating only with $NaN_3$, 10.4% and $K_2CO_3$, 2.4% as in Table 3

EXAMPLES XLVII-LI

Release Rate of Azide Ion

The following examples of Table 6 illustrate the slow release rate of azide ion from the compositions of this invention. The following procedure was used, and is often referred to as the Sutherland Test Method.

A Whatsman No. 41 filter paper disc, 9 centimeters in diameter was placed into a 10 centimeter petri dish and moistened with one (1) milliliter of deionized water. A batch of granules having 6.5 milligrams of azide ions per batch was distributed in the paper. The dish was covered and left covered for one half (½) hour. After uncovering the dish, both granules and filter paper were dried. The released azide ion was dissolved from the paper with 50 milliliters of deionized water, and the extract was collected in a volumetric flask containing 10 millicentimeters) fitted with a Whatsman glass fiber filter paper GS-(equivalent to No. 42 paper). The buchner funnel was placed on an aspirator bottle and a slight vacuum was applied, then 200 cubic centimeters (cc) of water were added to the funnel in aliquots of 10 cubic centimeter portions, which portions were allowed to drain, (simulated irrigation conditions). After all of the water (200 cc) had been added, the granules were air dried and stored. Visible observations were made to determine if the granules disintegrated, that is broke up and formed mud or clay like particles.

EXAMPLE LII

One gram of granules, Example XI (Table 2), impregnated with ferrous chloride ($FeCl_2$) when tested as described above, showed no disintegration.

EXAMPLE LIII

One gram of granules, Example XII (Table 2), which were impregnated with ferric chloride (FeCl$_3$) showed no disintegration when tested as described above.

EXAMPLE LIV

One gram of the azide granules, Example XIII (Table 2), which were impregnated with manganous chloride (MnCl$_2$), showed no disintegration when tested as described above.

EXAMPLE LV

One gram of the azide granules Example XIV (Table 2), which were impregnated with zinc chloride (ZnCl$_2$), showed no disintegration when tested as described above.

EXAMPLE LVI

One gram of the azide granules to which no other additives had been added, Example XLIV (Table 5), completely disintegrated into very fine grain-like colloids which began to pass through the filter, when only 20 cc of water had been added.

EXAMPLE LVII

One hundred (100) grams of granules 16/36 mesh, AARVM attapulgite clay (Engelhard Minerals and Chemical Division) were impregnated as described previously for the examples of Table 2 with a 15 cc aqueous solution containing 8.4 grams of anhydrous zinc chloride (ZnCl$_2$). The granules had no added azide. The ratio of the number of mole equivalents of azide ions to mole equivalents of zinc was zero.

One gram of these granules showed disintegration when tested as described above.

EXAMPLES LVIII–LX

Bioactivity of the Compositions

The following examples illustrate the bioactivity of solid compositions of azide-metal salt. The following test procedure was used.

Oat kernels were boiled in water for 15 to 20 minutes, drained, autoclaved, placed in an Erlenmeyer flask, and inoculated with agar grown mycelia of the pathogenic fungus *Sclerotium rolfsii*. The inoculated kernels were incubated for 7 to 10 days and periodically shaken during incubation to insure uniform growth of the fungus upon the kernels. After incubation, these kernels were spread out to air dry and then stored in a plastic bag in the dark at 4° Centigrade. (Under these conditions, the inoculated kernels keep for years.)

About 50 cubic centimeters of moist natural soil (taken from soil about the agricultural fields of Auburn University, Auburn, AL) was spread out and flattened within a plastic petri dish (diameter - 9.0 centimeters). Five of the inoculated kernels was placed upon the soil in a radial pattern, one kernel in the center of the dish and the other four equidistant from the center kernel and the rim of the petri dish. Each kernel was considered as a replicate for purposes of the test.

A pre-determined amount of the dried stored granule which had been tested in accordance with the disintegration test procedure mentioned herein was scattered over the soil surface and kernels in the petri dish at a rate corresponding to 8 to 12 lbs. per acre of sodium azide. The petri dish was covered and incubated for seven (7) days, during which time visible observations were made to determine if the colonies of *Sclerotium rolfsii* were controlled, that is killed, and if colonies of *Trichoderma veride* were increased. The saprophytic fungus *Trichoderma veride* indirectly controls the other pathogens, particularly, *Rhizoctonia* and *Pythium*, by removing their food supply or by producing antibiotics which effect these species; J. S. Warcup, "Soil and Fertilizers", Vol. XX, No. 1, (1957), pages 1 to 10.

EXAMPLE LVIII

The dried granules containing NaN$_3$, and ZnCl$_2$, from Example LV, were applied at the rate of 10 lbs. per acre of sodium azide to the inoculated petri dish in accordance with the bioactivity test procedure described above. These granules caused the *Sclerotium rolfsii* colonies to be completely controlled, while the colonies of *Trichoderma veride*, increased in population by over 100%.

EXAMPLE LIX

The dried granules containing sodium azide only, from Example LVI, were applied at the rate of 10 lbs. per acre of sodium azide as in Example LVIII. There was no control over *Sclerotium rolfsii*, nor was there an increase in *Trichoderma veride*.

EXAMPLE LX

The dried attapulgite clay granules impregnated with zinc chloride only, from Example LVII, were applied at the rate of 10 lbs. per acre of sodium azide as in Example LVIII. There was no control over *Sclerotium rolfsii*, nor was there an increase in growth of *Trichoderma veride*.

APPLICATION a. Factors Effecting Application

The ratio of the mole equivalents of azide ions to mole equivalents of the metal ion in the composition, as shown by the preceeding examples, for these novel compositions is important. By varying this ratio, the release rate of the azide ions can be tailored to cope with agricultural conditions such as wetness, soil type, irrigation conditions, or other environmental conditions which influence the effectiveness of azide ions against plant pests. The selection of this ratio results in optimum use of the azide salt and other salts in the compositions to combat plant pests, such as pathogenic microorganisms, pathogenic fungi, etc., or to add a synergistic effect against the plant pests.

The compositions of this invention are particularly useful for controlling plant pests, such as pathogenic fungi, pathogenic nemas, or other pathogenic microorganisms. The most preferred compositions for controlling plant pests are those containing zinc or magnesium, or both zinc and magnesium. The preferred ratio of mole equivalents of azide ions to mole equivalents of azide ions in these compositions used to control plant pests is from 0.8 to 2.0, and from 0.9 to 1.2 is especially preferred.

It should be noted that care must be used in the applications against pathogenic pests in that beneficial micro-flora, such as *Rhizobium japonium* (a nitrogen fixing bacterium) are not destroyed. However, where such beneficial micro-flora are not present, or if such beneficial micro-flora increases faster than pathogenic micro-flora, then the composition of this invention may be used without concern that the area will be made barren of beneficial micro-flora. If it is necessary to reestablish such beneficial micro-flora, this may be done by inoculation or other techniques for starting colonies of the beneficial micro-flora.

Control of Pathogenic Fungi

Fungi are controlled, that is their growth is inhibited when the compositions of this invention are applied at rates which give from 200 ppm to 1000 ppm of total azide ion to the surfaces of seeds, plants, or plant parts such as tubers, rhizomes, etc., preferably from 300 ppm to 800 ppm and especially preferred is from 500 ppm to 600 ppm. In applying the compositions to the soil to control pathogenic fungi, the useful range of application is from 200 ppm to 1000 ppm of azide ion (based on weight of soil into which the azide ion is incorporated). The preferred range is from 300 to 800 ppm, and especially preferred is from 500 to 600 ppm. When incorporated into the soil, a short period of time may be required before planting seeds which are sensitive to azide ion. The period of time depends upon the type of soil, and the temperature of the soil. When temperatures are about 4° C. to 10° C., the period of time may be from 5 to 25 days, but at 35° C., the period of time may be from 2 to 9 days, when the azide ion incorporated into the soil is at 1000 ppm. One can use higher amounts of the compositions to insure complete control of fungi, and other pathogens, provided the soil is left to air out before planting seeds and crops sensitive to azide.

The following fungi are specific examples of soil borne and air borne fungi effectively controlled by the compositions of this invention: *Alternaria tenuis, Aspergillus amstelodami, Aspergillus flavus, Aspergillus niger, Aspergillus ochraceus, Aspergillus ruber, Aspergillus tamarii, Colletotrichum graminicola, Diplodia macrospora, Diplodia zeae, Epicoccum nigrum, Fomes annosus, Fusarium moniliforme, Fusarium oxysporum* f. sp. *lycopersici, Fusarium oxysporum* f. sp. *nivum, Fusarium oxysporum* f. sp. *vasinfectum, Fusarium roseum, Gibberella zeae, Gloeosporium* sppp., *Gliocladium virens, Glomerella cingulata, Helminthosporium carbonum, Helminthosporium maydis, Helminthosporium turcicum, Macrophomina phaseola, Malanconium fuliginem, Metarrhizium anisopliae, Monilinia fructicola, Mortierella ramannianus, Mucor pusillus, Nigrospora oryzae, Ophiobolus* spp., *Penicillium citrinum, Penicillium corymbiferum, Penicillium decumbens, Penicillium frequentans, Penicillium implicatum, Phymatotrichum omnivorum, Phytophthora parasitica, Phythium aphanidermatum, Phythium debaryanum, Phythium deliense, Phythium ultimum, Rhizoctonia solani, Sclerotinia sclerotiorum, Thielavia terricola, Thielaviopis basicola, Trichoderma koingi, Verticillium albo-atrum,* and *Zygorhynchus moelleri.*

Control of Pathogenic Nematodes

Pathogenic nematodes are controlled by application of the compositions of this invention at rates from 1 to 500 ppm of the total azide ion in the composition based on dry weight of soil into which the compositions are incorporated. Preferably the rate is from 15 to 200 ppm, and especially preferred are rates from 15 to 100 ppm. It is preferred that the soil pH be within the range from 4.0 to 9.0, preferably from 5.0 to 8.0, and that the temperature of the soil during this application is from 4° Centigrade to 30° Centigrade, preferably from 15° Centigrade to 25° Centigrade.

Some examples of specific pathogenic nematodes controlled by the compositions of this invention are: *Heticotylenchus dihystra, Meloidogyne arenaria, Meloidogyne hapla, Meloidogyne incognita, Meloidogyne javanica, Heterodera glycines, Trichoderus christiei, Tylenchorhynchus claytoni, Scutellonema brachyrum, Xiphinema americanum, Pratylenchus zeae, Belonolaimus* spp., *Tylenchorhynchus* spp., and *Scutellonema brachyurum.*

Control of Pathogenic Bacteria and Other Plant Pests

Other plant pests such as bacteria both gram negative and gram positive are controlled by applying the compositions at rates from 1 to 500 ppm of total azide ion to the plants, plant parts, or soil to control bacteria effecting the leaves, stems, roots, crown, seeds, tubers, rhizomes, or other hardy plant parts. Preferably the rate of application is from 15 to 400 ppm, with 20 to 100 ppm being the usual rate for application to plants, while from 500 to 2000 ppm per weight of dry soil is preferred for soil applications.

Examples of specific bacteria which may be controlled are gram negative bacteria of *Agrobacterium tumefacius* (crown gall), *Erwinia carotovora, Pseudomonas lachrymans* (angular leaf spot), *Pseudomonas solanacearum* (bacterial wilt), *Xanthomonas malvacearum* (bacterial blight), and gram positive bacteria of *Corynebacterium michiganense* (bacteria canker).

Examples of other diseases and pathogenic plant pests which may be controlled when the compositions are applied at the rates mentioned herein are *Pseudomonas phaseolica* (bacterial blight), Collar rot of peanuts, *Cylindrocladium crotolariae* (black rot of peanuts), *Phytophthora phaesoli* (downy mildew of lima bean), *Pseudoperonospera cubensis* (downy mildew of cucumbers), *Phytophthora capsici* (blight of pepper), *Sclerotium* spp., particularly *Sclerotium rolfsii* Sacc. (stem rot, blight of tomatoes) at rates between 500 ppm and 2000 ppm of azide per weight of dried soil, *Diplocarpon rosae* (black spot of rose), *Sphaerotheca pannosa* var. (rosae) (powdery mildew of roses), grape root borer, rice eater weevil, *Phytophthora infestans, Pseudoperonospora cubensis, Cercospora apii, Septoria apii, Botrytis* spp., *Colletotrichum lindemuthianum, Uromyces phaseoli,* mites, such as *Tetranychus* spp., in particular *Tetranychus telarius, Coccomyces hiemalis,* beetles such as *Epilochna* spp., in particular *Epilachna varivestis, Popillia japonica, Aceria neocynodomis, Blissus leucopterus insularis,* fruit fungi such as *Gymnosporangium juniperivirginianae, Venturia inaequolis, Podosphaera leucotricha, Plasmopara viticola, Uncinula necastor, Botrytis civerea, Piricularia oryzae,* and *Diplocarpon rosae.*

Methods of Applying Compositions

This control (substantial reduction in the deleterious effects of the plant pests) is effected by applying an effective amount of these compositions to the region where these pests such as fungus or other organisms dwell so as to bring the azide-metal salt in contact with the pest. The region may be the soil, the plant itself, the pest itself, the fungus itself, the organism itself, or any combination thereof. The phrase "applying these compositions" refers to any manner of application; such as applying the azide-metal salts in a spray, e.g., liquid compositions mentioned herein, or as a dust of the solid compositions mentioned herein. The application may be done as a protectant application, that is, prior to the plant or soil becoming infested with the pest, such as the fungus or organism; or as an eradicant application, that is, after the plant or soil has been infested with the pest.

In using the compositions of this invention to contact the region one may apply the metal salt and the azide, concurrently to the region, e.g., the liquid compositions, or the solid compositions mentioned herein, or one may apply the metal salt first, as granules of the metal salt or as liquid compositions of the metal salts, and then the azide, as azide granules or as liquid compositions of the azide mentioned herein, or one may apply the azide first and then the metal salt. It is preferred that both are applied concurrently.

Application of Liquid Compositions

In application of liquid compositions against the plant pests hereinbefore mentioned, a solution containing the metal salt may be applied first to the region, and then a solution containing the azide may be applied afterwards, generally, within one hour. When applied to plants, or plant pests, the liquid compositions are applied to the dripping point. The effective amount of the liquid composition for application to the plant or fungus to the dripping point may have a range of total azide ion in the liquid composition from 5000 parts per million (ppm) by weight of azide ion to 100 ppm. Generally the range is from 2000 ppm to 200 ppm, but preferably this range is from 1000 ppm to 200 ppm, and especially useful is the range from 800 ppm to 300 ppm. The preferred ratio of mole equivalents of azide ions to mole equivalents of metal ions in the liquid composition is from 0.8 to 2.0, and zinc and magnesium salts are preferred for these solutions. These liquid compositions are effective against the plant pests mentioned hereinbefore.

Other methods of applying the liquid composition to plants and parts, are by dipping or coating of tubers, or seeds, such as oats and wheat with dusts containing the compositions, or by wetting the parts, such as seeds with solutions containing the compositions.

EXAMPLES LXI-LXIV

The following examples illustrate the use of liquid compositions to prevent molding of oat seeds and wheat seeds during storage.

EXAMPLE LXI

Wheat seeds (100 grams) were placed in a jar which contained 4.0 grams of an aqueous solution in which 2.5 milligrams of potassium azide ($KN_3$), and 21 milligrams of anhydrous zinc chloride ($ZnCl_2$), were dissolved. The jar was rotated until the seeds were uniformly coated with the solution, at room temperature. The seeds were removed from the jar, and spread out in shallow metal trays to air dry for several hours. The seeds were then stored at room temperature in open plastic bags for 2 months under normal storage conditions for wheat seeds. The seeds were not molded after this period. Upon planting under greenhouse conditions, the seeds had 95% germination.

EXAMPLE LXII

Oat seeds (100 grams) were coated as in Example LXI with 4.0 grams of an aqueous solution containing 5 milligrams of potassium azide and 42 milligrams of anhydrous zinc chloride ($ZnCl_2$). These seeds were stored for 2 months under normal storage conditions in open bags. The seeds were not molded after this period. Upon planting under greenhouse conditions, the seeds had 98% germination.

EXAMPLE LXIII

Uncoated wheat seeds stored under the conditions of Example LXI developed mold, when planted under the same conditions as in LXI they had only 50% germination.

EXAMPLE LXIV

Uncoated oat seeds stored under the conditions of Example LXII developed mold, and had only 40% germination when planted under the same conditions as in Example LXII.

Application of Solid Compositions

When contact is to the soil itself or the fungi or organism itself, by the solid compositions of this invention, the rate of application will vary. The application rate depends upon the soil composition - sandy soils requiring less than high organic clay soils, and upon the type of nematode or fungi to be controlled. The rate of application to give the effective amount of the compositions may be from 0.5 to 500 lbs. of azide ion (total azide ion) per acre per inch depth of the soil. Generally the rate is from 10 to 100 lbs. of azide ion per acre, but preferably the rate is from 10 to 50 lbs. of azide ion per acre per inch of soil under optimum conditions.

The solid compositions of this invention are particularly useful in agricultural applications. For example, Florida begger weed (*Desmodium Tortuosum*) in a crop field of peanuts is controlled by applying the granules to the soil at a rate which gives 20 lbs. of sodium azide per acre per inch of soil. Other uses of the granules are to control plant pests of nematodes, nematode eggs, other weeds, as set forth in the patents of McConnell et al; such as U.S. Pat. Nos. 3,376,125, 3,376,126, and 3,376,127, when applied at the upper range of rates mentioned hereinbefore.

These compositions may also be applied to augment the growth of beneficial micro-flora such as *Trichoderma viride*, and various predatory nemas, which are biological control agents of plant pests, while controlling the plant pests.

While the invention has been described with reference to specific details of certain illustrative embodiments, it is not intended that it shall be limited thereby except in so far as such details appear in the accompanying claims.

I claim:

1. A composition suitable for agriculture which is a physical mixture having the property of dissolving in a suitable solvent to form a solution, said composition comprised of granules of an azide and granules of a metal salt; said azide being selected from the group consisting of alkaline earth metal azide, alkali metal azide, and mixtures thereof, and said metal salt being selected from the group consisting of metal salts having a metal ion selected from the group consisting of aluminum, iron (II), cobalt (II), nickel, tin (II), magnesium, zinc, and manganese (II), and an anion selected from the group consisting of bromide, chloride, fluoride, carbonate, hydroxide, phosphate, sulfate, formate, acetate, propionate, butyrate, oxalate, citrate, malate, lactate, and tartrate; the respective amounts of said axide granules and said metal salt granules in the mixture being such that when said mixture is dissolved in said solvent to form the solution, there exists in the solution a ratio of mole equivalents of azide ion to mole equivalents of metal ion within the range of 0.1 to 8.0 and said solution having the property that it is less phytotoxic than a solution having the same amount of azide ion but none of the metal salt therein; and said composition being substantially free from substances which decompose the azide.

2. The composition of claim 1, wherein the azide is selected from the group consisting of sodium azide, potassium azide, and mixtures thereof.

3. The composition of claim 2, wherein the metal salt is selected from the group consisting of metal salts having an anion selected from the group consisting of bromides, chloride, sulfates, and nitrates and a metal ion selected from the group consisting of iron (II), cobalt (II), magnesium, manganese (II), nickel, tin (II), and zinc.

4. The composition of claim 2, wherein the metal salt is selected from the group consisting of magnesium chloride, magnesium bromide, magnesium nitrate, magnesium sulfate, zinc bromide, zinc chloride, zinc nitrate, zinc sulfate, and mixtures thereof.

5. The composition of claim 2, wherein said ratio of mole equivalents of azide ion to mole equivalents of metal ion is within the range from 0.8 to 2.0.

6. The composition of claim 1, which further comprises a basic azide stabilizing material selected from the group consisting of sodium hydroxide, potassium hydroxide, potassium carbonate, sodium carbonate, and mixtures thereof, said basic azide stabilizing material being within the range of 0.1 to 10 weight percent of the azide in the mixture.

7. The composition of claim 3, which further comprises a basic azide stabilizing material selected from the group consisting of sodium hydroxide, potassium hydroxide, potassium carbonate, sodium carbonate, and mixtures thereof, said basic azide stabilizing material being within the range of 0.1 to 10 weight percent of the azide in the mixture.

8. The composition of claim 5, which further comprises a basic azide stabilizing material selected from the group consisting of sodium hydroxide, potassium hydroxide, potassium carbonate, sodium carbonate, and mixtures thereof, said basic azide stabilizing material being within the range of 0.1 to 10 weight percent of the azide in the mixture.

9. A composition suitable for agriculture comprised of an azide in chemical combination with a metal salt which azide and metal salt chemical combination are in chemical combination with a granule of an inert material which is impregnated with the azide and metal salt, said azide being selected from the group consisting of hydrazoic acid, alkali metal azide, alkaline earth metal azide, and mixtures thereof, said metal salt being selected from the group consisting of metal salts having a metal ion selected from the group consisting of aluminum, magnesium cobalt (II), iron (II), iron (III), nickel, manganese (II), tin (II), and zinc, and an anion selected from the group consisting of bromide, chloride, fluoride, carbonate, sulfate, phosphate, nitrate, hydroxide, oxide, formate, acetate, propionate, oxalate, malate, citrate, butyrate, lactate, and tartrate, except that when the anion is oxide or hydroxide then the azide is selected from the group consisting of alkali metal azide and alkaline earth metal azides; said inert material being a material which disintegrates within a few weeks within the soil to form materials in which plants may be grown or otherwise is disposed of in the soil without adverse effect on plant life grown therein; said composition having a ratio of mole equivalents of azide ions to mole equivalent of metal ions within the range of 0.01 to 8.0, and said composition being substantially free from substances which decompose the azide.

10. The composition as recited in claim 9, wherein the inert material is selected from the group consisting of attapulgite, montmorillonite, kaolite, and bentonite.

11. The composition as recited in claim 10, wherein the azide is selected from the group consisting of sodium azide, potassium azide, and mixtures thereof.

12. The composition as recited in claim 11, wherein the ratio of mole equivalents of azide ions to mole equivalents of metal ions is within the range of 0.8 to 2.0.

13. The composition as recited in claim 12, which further comprises a basic azide stabilizing material selected from the group consisting of sodium hydroxide, potassium hydroxide, sodium carbonate, potassium carbonate, and mixtures thereof, the weight percent of said azide stabilizing material being within the range of 0.1 to 10 weight percent of azide in the composition.

14. The composition as recited in claim 11, wherein the metal salt is selected from the group consisting of metal salts having an anion selected from group consisting of bromide, chloride, sulfate, and nitrate, and a metal ion selected from group consisting of iron (II), cobalt (II), magnesium, manganese (II), nickel, tin (II), and zinc.

15. The composition as recited in claim 11, wherein the metal salt is selected from the group consisting of magnesium chloride, magnesium nitrate, magnesium sulfate, zinc chloride, zinc nitrate, zinc sulfate, and mixtures thereof.

16. The composition as recited in claim 15, wherein the ratio of the mole equivalents of azide ions to the mole equivalents of metal ions is within the range of 0.8 to 2.0.

17. The composition as recited in claim 15, wherein the ratio of the mole equivalents of azide ions to the mole equivalents of metal ions is within the range of 0.9 to 1.2, and said azide stabilizing material is potassium carbonate.

18. A composition suitable for agriculture comprised of an inert material selected from the group consisting of attapulgite, and montmorillonite, impregnated with an azide and a metal salt which azide and metal salt are in chemical combination, said azide being selected from the group consisting of sodium azide, postassium azide, and mixtures thereof, said metal salt being selected from the group consisting of magnesium chloride, magnesium sulfate, magnesium nitrate, zinc chloride, zinc nitrate, zinc sulfate, and mixtures thereof, and the respective amount of azide and metal salt is such that the ratio of the mole equivalents of azide ion to mole equivalents of metal ion is within the ratio of 0.8 to 2.0; said composition being substantially free from substances which cause decomposition of the azide.

19. The composition as recited in claim 18, which further comprises a basic azide stabilizing material selected from the group consisting of sodium carbonate, sodium hydroxide, potassium carbonate, potassium hydroxide, and mixtures thereof.

20. A granular composition suitable for agriculture comprised of an azide in chemical combination with a metal salt, said azide being selected from the group consisting of alkaline earth metal azides, and alkali metal azides, and said metal salt being selected from the group consisting of metal salts having a metal ion selected from the group consisting of aluminum, magnesium, iron (II), iron (III), cobalt (II), nickel, manganese (II), tin (II), and zinc, and having an anion selected from the group consisting of acetate, bromide, chloride, fluoride, nitrate, sulfate, phosphate, hydroxide, oxide, carbonate, formate, propionate, butyrate, tartrate, oxalate, malate, citrate, and lactate, said composition having a ratio of mole equivalents of azide ion to mole equivalents of metal ion within the range of 0.1 to 8.0, said composition being substantially free from substances which cause decomposition of the azide.

21. The solid composition as recited in claim 20, wherein the azide is selected from the group consisting of sodium azide, potassium azide, and mixtures thereof.

22. The solid composition as recited in claim 21, wherein the ratio of mole equivalents of azide ion to mole equivalents of metal ion is within the ratio of 0.9 to 1.2

23. The solid composition as recited in claim 22, wherein the metal salt is selected from the group consisting of magnesium chloride, magnesium nitrate, magnesium sulfate, zinc chloride, zinc nitrate, zinc sulfate, and mixtures thereof.

24. The solid composition as recited in claim 23, which further comprises a basic azide stabilizing material selected from the group consisting of sodium hydroxide, potassium hydroxide, sodium carbonate, potassium carbonate, and mixtures thereof, the weight percent of said basic azide stabilizing material being within the range of 0.1 to 10 weight percent of the azide in the composition.

25. A granule suitable for agriculture comprised of particles of at least one azide in combination with and physically in contact with particles of at least one metal salt, said particles being bonded to one another to form a granule having a size from 100 mesh to 6 mesh, a low tendency to form dust and a good resistance to attrition as evidenced by a friability value of less than 5 percent, said azide being selected from the group consisting of alkali metal azide and alkaline earth metal azide, and said metal salt being selected from the group consisting of those salts having a metal ion selected from the group consisting of aluminum, magnesium, iron (II), iron (III), nickel, cobalt (II), manganese (II), tin (II), and zinc, and a anion selected from the group consisting of bromide, chloride, fluoride, nitrate, sulfate, phosphate, carbonate, oxide, hydroxide, acetate, formate, propionate, butyrate, oxalate, citrate, lactate, malate, and tartrate, said composition being substantially free from substances causing decomposition of the azide; and said composition having a ratio of mole equivalents of azide ion to mole equivalents of metal ion within the range of 0.1 to 8.0.

26. The composition as recited in claim 25, which further comprises a binder material selected from the group consisting of alkali metal silicates, alkaline earth metal silicates, dextrin, and polyvinyl alcohol, said binder constituting from 0.2 to 10 weight percent of the composition.

27. The composition as recited in claim 25, which further comprises a diluent which is an alkali metal halid, and diluent constituting from 1 to 25 weight percent of the composition.

28. The composition as recited in claim 26, which further comprises a diluent which is an alkali metal halides, said diluent constituting from 1 to 25 weight percent of the composition.

29. The composition as recited in claim 28, which further constitutes a basic azide stabilizing material selected from the group consisting of potassium hydroxide, potassium carbonate, sodium hydroxide, sodium carbonate, and mixtures thereof, said material constituting from 0.5 to 10 weight percent of the azide in the composition.

30. The composition as recited in claim 26, wherein the azide is selected from the group consisting of sodium azide, potassium azide, and mixtures thereof.

31. The composition as recited in claim 30, wherein the metal salt is selected from the group consisting of magnesium chloride, magnesium nitrate, magnesium sulfate, zinc chloride, zinc nitrate, zinc sulfate, and mixtures thereof.

32. The composition as recited in claim 31, wherein the diluent is selected from the group consisting of sodium chloride and potassium chloride.

33. The composition as recited in claim 32, wherein the binder is sodium silicate.

34. The composition as recited in claim 33, which further comprises a basic azide stabilizing material selected from the group consisting of potassium carbonate, and potassium hydroxide, said basic azide stabilizing material constituting from 0.5 to 10 weight percent of the azide in the composition.

35. A liquid composition suitable for agriculture comprised of an azide in combination with a metal salt in a solvent which dissolves the azide and the metal salt; said azide being selected from the group consisting of hydrazoic acid, alkali metal, and alkaline earth metal azides, and mixtures thereof, said metal salt being selected from the group consisting of those salts having a metal ion selected from the group consisting of cobalt (II), iron (II), manganese (II), magnesium, zinc, and tin (II), and an anion selected from the group consisting of choride, bromide, fluoride, sulfate, nitrate, formate, citrate, malate, acetate, and propionate; the ratio of mole equivalents of azide ions to mole equivalents of metal ions in the liquid composition being within the range from 0.01 to 8.0, said composition being substantially free from substances causing decomposition of the azide, and having from 200 ppm of azide ion to the maximum amount solubilized by the solvent of the composition, and having the property of being less phytotoxic than a liquid composition with the same amount of azide but without the metal salt.

36. A method of controlling plant pests of pathogenic fungi nematodes and bacteria which comprises contacting the region wherein the plant pest dwells with an effective amount of a composition to control said plant pest, said composition being a physical mixture comprised of granules of an azide and granules of a metal salt which mixture has the property of dissolving in water, said azide being selected from the group consisting of alkaline earth metal azide, alkali metal azide, and mixtures thereof, and said metal salt being selected from the group of metal salts having a metal ion selected from the group consisting of aluminum, iron (II), cobalt (II), nickel, tin (II), magnesium, zinc, and manganese (II), and an anion selected from the group consisting of bromide, chloride, fluoride, carbonate, hydroxide, oxide, phosphate, sulfate, formate, acetate, propionate, butyrate, oxalate, citrate, malate, lactate, and tartrate; the respective amounts of said azide and said metal salt in the mixture being such that when said mixture is dissolved in the water there exists in the water a ratio of mole equivalents of azide ion to mole equivalents of metal ion from the metal salt within the range of 0.01 to 8.0, and said composition being substantially free from substances which decompose the azide.

37. The method of claim 36, wherein the azide is selected from the group consisting of sodium azide, potassium azide, and mixtures thereof.

38. The method of claim 37, wherein the metal salt is selected from the group consisting of metal salts having an anion selected from the group consisting of bromide, chloride, sulfate, and nitrate and a metal ion selected from the group consisting of iron (II), cobalt (II), magnesium, manganese (II), nickel, tin (II), zinc, and mixtures thereof.

39. The method of claim 37, wherein the metal salt is selected from the group consisting of magnesium chloride, magnesium bromide, magnesium nitrate, magnesium sulfate, zinc bromide, zinc chloride, zinc nitrate, zinc sulfate, and mixtures thereof.

40. The method of claim 39, wherein said ratio of mole equivalents of azide ion to mole equivalents of metal ion is within the range from 0.8 to 2.0.

41. The method of claim 36, which further comprises a basic azide stabilizing material selected from the group consisting of sodium hydroxide, potassium hydroxide, potassium carbonate, sodium carbonate, and mixtures thereof, said basic azide stabilizing material being within the range of 0.1 to 10 weight percent of the azide in the mixture.

42. The method of claim 38, which further comprises a basic azide stabilizing material selected from the group consisting of sodium hydroxide, potassium hydroxide, potassium carbonate, sodium carbonate, and mixtures thereof, said basic azide stabilizing material being within the range of 0.1 to 10 weight percent of the azide in the mixture.

43. The method of claim 40, which further comprises a basic azide stabilizing material selected from the group consisting of sodium hydroxide, potassium hydroxide, potassium carbonate, sodium carbonate, and mixtures thereof, said basic azide stabilizing material being within the range of 0.1 to 10 weight percent of the azide in the mixture.

44. A method of controlling plant pests of pathogenic fungi nematodes, and bacteria which comprises contacting the region wherein the plant pest dwells with an effective amount of a composition to control said plant pest, said composition being a granular composition of an azide in chemical combination with a metal salt which are in chemical combination with a granule of an inert material which is impregnated with the azide and metal salt, said azide being selected from the group consisting of alkali metal azide, alkaline earth metal azide, and mixtures thereof, said metal salt being selected from the group of metal salts consisting of those having a metal ion selected from the group consisting of aluminum, magnesium, cobalt (II), iron (II), iron (III), nickel, manganese (II), tin (II), and zinc, and an anion selected from the group consisting of bromide, chloride, fluoride, carbonate, sulfate, phosphate, nitrate, hydroxide, oxide, formate, acetate, propionate, oxalate, malate, citrate, butyrate, lactate, and tartrate, said inert material being a material which disintegrates within a few weeks within the soil to form materials in which plants may be grown or otherwise is disposed of in the soil without adverse effect on plant life grown therein, said composition having a ratio of mole equivalents of azide ion to mole equivalents of metal ion within the range of 0.01 to 8.0, and said composition being substantially free from substances which decompose the azide.

45. The method as recited in claim 44, wherein the inert material is selected from the group consisting of attapulgite, montmorillonite, kaolite, and bentonite.

46. The method as recited in claim 45, wherein the azide is selected from the group consisting of sodium azide, potassium azide, and mixtures thereof.

47. The method as recited in claim 46, wherein the ratio of mole equivalents of azide ion to mole equivalents of metal ion is within the range of 0.8 to 2.0.

48. The method as recited in claim 47, which further comprises a basic azide stabilizing material selected from the group consisting of sodium hydroxide, potassium hydroxide, sodium carbonate, potassium carbonate, and mixtures thereof, the weight percent of said azide stabilizing material being within the range of 0.1 to 10 weight percent of azide in the composition.

49. The method as recited in claim 46, wherein the metal salt is selected from the group consisting of metal salts having an anion selected from the group consisting of bromide, chloride, sulfate, and nitrate, and a metal ion selected from the group consisting of iron (II), cobalt (II), magnesium, manganese (II), nickel, tin (II), and zinc.

50. The method as recited in claim 46, wherein the metal salt is selected from the group consisting of magnesium chloride, magnesium nitrate, magnesium sulfate, zinc chloride, zinc nitrate, zinc sulfate, and mixtures thereof.

51. The method as recited in claim 50, wherein the ratio of mole equivalents of azide ion to mole equivalents of metal ion is within the range of 0.8 to 2.0.

52. The method as recited in claim 50, wherein the ratio of mole equivalents of azide ion to mole equivalents of metal ion from the metal salt is within the range of 0.9 to 1.2, and said azide stabilizing material is potassium carbonate.

53. A method of controlling plant pests of pathogenic fungi, nematodes, and bacteria which comprises contacting the region wherein the plant pest dwells with an effective amount of a composition to control said plant pest, said composition being a granular composition comprised of an azide in chemical combination with a metal salt, said azide being selected from the group consisting of alkaline earth metal azides, and alkali metal azide, and said metal salt being selected from the group consisting of metal salts having a metal ion selected from the group consisting of aluminum, magnesium, ion (II), iron (III), cobalt (II), nickel, manganese (II), tin (II), and zinc, and having an anion selected from the group consisting of acetate, bromide, chloride, fluoride, nitrate, sulfate, phosphate, hydroxide, oxide, carbonate, formate, propionate, butyrate, tartrate, oxalate, malate, citrate, and lactate, said composition having a ratio of mole equivalents of azide ion to mole equivalents of metal ion within the range of 0.1 to 8.0, and said composition being substantially free from substances which cause decomposition of the azide.

54. The method as recited in claim 53, wherein the azide is selected from the group consisting of sodium azide, potassium azide, and mixtures thereof.

55. The method as recited in claim 54, wherein the ratio of mole equivalents of azide ion to mole equivalents of metal ion is within the range of 0.9 to 1.2.

56. The method as recited in claim 55, wherein the metal salt is selected from the group consisting of magnesium chloride, magnesium nitrate, magnesium sulfate, zinc chloride, zinc nitrate, zinc sulfate, and mixtures thereof.

57. The method as recited in claim 56, which further comprises a basic azide stabilizing material selected from the group consisting of sodium hydroxide, potassium hydroxide, sodium carbonate, potassium carbonate, and mixtures thereof, the weight percent of said basic azide stabilizing material being within the range of 0.1 to 10 weight percent of the azide in the composition.

58. A method of controlling plant pests of pathogenic fungi, nematodes, and bacteria which comprises contacting the region wherein the plant pest dwells with an effective amount of a composition to control said plant pest, said composition being a granule comprised of particles of at least one azide in combination with and physically in contact with particles of at least one metal salt, said particles being bonded to one another to form granules having a size from 100 mesh to 6 mesh, said granule having a low tendency to form dust and a good resistance to attrition as evidenced by a friability value of less than 5 percent, said azide being selected from the group consisting of alkali metal azide and alkaline earth metal azide, and said metal salt being selected from the group consisting of those salts having a metal ion selected from the group consisting of aluminum, magnesium, iron (II), iron (III), nickel, cobalt (II), manganese (II), tin (II), and zinc, and an anion selected from the group consisting of bromide, chloride, fluoride, nitrate, sulfate, phosphate, carbonate, oxide, hydroxide, acetate, formate, propionate, butyrate, oxalate, citrate, lactate, malate, and tartrate, said composition being substantially free from substances causing decomposition of the azide; and said composition having a ratio of mole equivalents of azide ion to mole equivalents of metal ion from the metal salt within the range of 0.1 to 8.0.

59. The method as recited in claim 58, which further comprises a binder material selected from the group consisting of alkali metal silicates, alkaline earth metal silicates, dextrin, or polyvinyl alcohol, said binder constituting from 0.2 to 10 weight percent of the composition.

60. The method as recited in claim 58, which further comprises a diluent selected from the group consisting of alkali metal halides, and mixtures thereof, said diluent constituting from 1 to 25 weight percent of the composition.

61. The method as recited in claim 60, which further comprises a diluent selected from the group consisting of alkali metal halides, and mixtures thereof, said diluent constituting from 1 to 25 weight percent of the composition.

62. The method as recited in claim 61, which further constitutes a basic azide stabilizing material selected from the group consisting of potassium hydroxide, potassium carbonate, sodium hydroxide, sodium carbonate, and mixtures thereof, said material constituting from 0.5 to 10 weight percent of the azide in the composition.

63. The method as recited in claim 59, wherein the azide is selected from the group consisting of sodium azide, potassium azide, and mixtures thereof.

64. The method as recited in claim 63, wherein the metal salt is selected from the group consisting of magnesium chloride, magnesium nitrate, magnesium sulfate, zinc chloride, zinc nitrate, zinc sulfate, and mixtures thereof.

65. The method as recited in claim 64, wherein the diluent is selected from the group consisting of sodium chloride, potassium chloride, and mixtures thereof.

66. The method as recited in claim 65, wherein the binder is sodium silicate.

67. The method as recited in claim 66, which further comprises a basic azide stabilizing material selected from the group consisting of potassium carbonate, and potassium hydroxide, said basic azide stabilizing material constituting from 0.5 to 10 weight percent of the azide in the composition.

68. A method of controlling plant pests of pathogenic fungi, nematodes, and bacteria which comprises contacting the region wherein the plant pest dwells with an effective amount of a composition to control said plant pest, said composition being a liquid composition comprised of an azide in combination with a metal salt in a solvent which dissolves the azide and the metal salt; said azide being selected from the group consisting of hydrazoic acid, alkali metal, and alkaline earth metal azides, said metal salt being selected from the group consisting of those salts having a metal ion selected from the group consisting of cobalt (II), iron (II), manganese (II), magnesium, zinc, and tin (II), and an anion selected from the group consisting of fluoride, chloride, bromide, sulfate, nitrate, formate, citrate, malate, acetate, and propionate; the ratio of mole equivalents of azide ions to mole equivalents of metal ions in the liquid composition being within the range of 0.01 to 8.0, said composition being substantially free from substances causing decomposition of the azide, and having from 200 ppm of azide ion to the maximum amount solubilized by the solvent of the composition.

69. The method as recited in claim 68, wherein the solvent is water.

70. The method as recited in claim 69, wherein the ratio of mole equivalents of azide ions to mole equivalents of metal ions from the metal salt is within the range from 0.8 to 1.5.

71. The method as recited in claim 70, wherein the azide is selected from the group consisting of sodium azide, potassium azide, and mixtures thereof.

72. The method as recited in claim 71, wherein the metal salt is selected from the group consisting of magnesium chloride, magnesium nitrate, magnesium sulfate, zinc chloride, zinc nitrate, zinc sulfate, and mixtures thereof.

* * * * *